United States Patent [19]
Qian et al.

[11] Patent Number: 6,052,476
[45] Date of Patent: Apr. 18, 2000

[54] METHOD AND APPARATUS FOR CONTROLLING X-RAY ANGIOGRAPHIC IMAGE ACQUISTION

[75] Inventors: Jianzhong Qian, Princeton Junction, N.J.; Ping Hua, Streamwood, Ill.; Zhenyu Wu, Plainsboro, N.J.

[73] Assignee: Siemens Corporate Research, Inc., Piscataway, N.J.

[21] Appl. No.: 09/251,243

[22] Filed: Feb. 16, 1999

Related U.S. Application Data

[62] Division of application No. 08/933,522, Sep. 18, 1997.

[51] Int. Cl.⁷ .............. G06K 9/00; G06K 9/40; A61B 6/04
[52] U.S. Cl. .............. 382/130; 382/132; 382/274; 378/98.12; 378/209
[58] Field of Search ............................ 382/128, 130, 382/132, 274; 378/98.12, 209

[56] References Cited

U.S. PATENT DOCUMENTS

| | | | |
|---|---|---|---|
| 4,862,359 | 8/1989 | Trivedi et al. | 600/544 |
| 5,123,056 | 6/1992 | Wilson | 382/132 |
| 5,315,631 | 5/1994 | Hillen et al. | 378/98.8 |
| 5,347,570 | 9/1994 | Haaks | 378/98.12 |
| 5,467,404 | 11/1995 | Vuylsteke et al. | 382/274 |
| 5,631,942 | 5/1997 | Shinoda | 378/98.12 |
| 5,644,646 | 7/1997 | Du et al. | 382/128 |
| 5,768,405 | 6/1998 | Makram-Ebeid | 382/128 |
| 5,832,134 | 11/1998 | Avinash et al. | 382/257 |
| 5,833,607 | 11/1998 | Chou et al. | 382/130 |
| 5,872,861 | 2/1999 | Makram-Ebeid | 382/130 |

FOREIGN PATENT DOCUMENTS

| | | | |
|---|---|---|---|
| 0088356A1 | 9/1983 | European Pat. Off. | H05G 1/64 |

*Primary Examiner*—Amelia Au
*Assistant Examiner*—Mehrdad Dastouri
*Attorney, Agent, or Firm*—Donald B. Paschburg

[57] ABSTRACT

Controlling the stepping of an x-ray angiography imaging device (and/or table), and/or providing a visualization aid for stepping an x-ray angiography imaging device (and/or table), to maximize the diagnostic usefulness of images acquired by the x-ray angiography imaging device. The stepping and visualization aid use features, extracted from captured images, of the state of contrast media injected into a patient.

14 Claims, 27 Drawing Sheets

DI global Max

DID global Max

METHOD AND APPARATUS FOR CONTROLLING X-RAY ANGIOGRAPHIC IMAGE ACQUISTION

This application is a Division of Ser. No. 08/933,522 filed Sep. 18, 1997.

BACKGROUND OF THE INVENTION a. Field of the Invention

The present invention concerns the control of an imaging device. More particularly, the present invention concerns controlling the stepping of an x-ray angiographic imaging device to maximize the diagnostic and/or therapeutic usefulness of images acquired by the x-ray angiographic imaging device, while minimizing contrast medium and x-ray dosages to the patient.

b. Related Art

X-ray imaging devices have been important tools for medical diagnosis and intervention. For example, x-rays have been used to observe the blood vessels of patients. Typically, a radiopaque (i.e., opaque to radiation) substance (also referred to as "contrast media" or "bolus") is injected into a blood vessel under consideration. The blood vessel can be imaged based on x-rays of the blood vessel containing the radiopaque substance. This practice is known as angiography.

FIG. 1a is a known angiographic system 100 for studying the blood vessels in the left leg 104 and the right leg 106 of a patient 102 laying on table 160. Contrast media is injected into a blood vessel of the patient 102 with the contrast media injection means 150. The blood vessels, through which the contrast media will flow, are irradiated with x-rays from x-ray generator 111 and an image of an area of the patient 102 is captured by x-ray detector 110. The image is provided to visual output unit 120. As the blood flows down the left and right legs 104 and 106, respectively, of the patient 102, the contrast media will be carried down through the blood vessels of the left and right legs 104 and 106, respectively.

Unfortunately, the contrast media has some adverse side effects. First, patients often experience discomfort, typically a burning sensation, when and after the contrast media is injected. The severity and length of such discomfort will increase as the amount of contrast media injected increases. Second, the contrast media may adversely affect a patient's kidneys. The extent of the affect of the contrast media on the patient's kidneys will depend on the patient's renal condition and on the amount of contrast media used. Accordingly, the amount of contrast media used should be minimized—only being used to the extent needed to provide diagnostically useful images of a patient's blood vessels.

Since the amount of contrast media is limited, as the contrast media passes through a given point of a blood vessel, the contrast of a corresponding image will increase (known as "wash-in" period), reach a period of maximum contrast (known as a "plateau" period), and then decrease (known as "wash-out" period). Thus, the imaging device, which includes x-ray generator 111 and x-ray detector 110, should image a section of the legs 104/106 of the patient 102 when the contrast media within that section of the legs 104/106 reaches the period of maximum contrast. As the contrast media flows down through the legs 104/106 of the patient 102, the imaging device 110/111 must be moved in the direction Y, indicated by arrow 135, by means of an imaging device stepper 130.

The x-ray generator 111 may be mechanically coupled, or controlled in unison, with the x-ray detector 110 such that both move together. The imaging device stepper 130 is controlled by step controller 140 which is operated by a medical professional (not shown). The medical professional (also referred to as "the operator" or "the angiographer") relies on the images provided by the visual output device 120 in judging when to command the image device stepper 130 to move the imaging device to a next position (also referred to as "gantry station(s)"). Since the imaging device stepper 130 cannot instantaneously move the imaging device 110/111 to the next station, a stepping time lag must be considered.

Unfortunately, due to limitations in human vision, reaction time, and judgment, the angiographer may command the imaging device stepper 130 to step the imaging device 110/111 too early or too late. If the imaging device 110/111 is stepped too early, the images acquired by the imaging device 110/111 will have been, and will be, acquired when the contrast fluid is in a wash-in period, before maximum contrast (or opacity) occurs. If, on the other hand, the imaging device 110/111 is stepped too late, the images acquired by the imaging device will be acquired after the contrast medium has reached maximum opacity—namely, either in "wash-out" period or a "plateau" period. If the image is acquired when the contrast fluid is in a "wash-out" period, after maximum contrast (or opacity) has occurred, the diagnostic usefulness of the acquired image will decrease. In addition, the patient 102 may be exposed to unnecessary extra x-ray dosage since frames acquired after the contrast medium has reached maximum opacity carry redundant information.

One way of maximizing the diagnostic usefulness of images acquired by the imaging device 110/111 would be to increase the amount of contrast media injected into a patient thereby increasing the (plateau) period of useful contrast between the wash-in and wash-out periods. By increasing the (plateau) period of useful contrast between the wash-in and wash-out periods, a greater margin of error in the stepping times is afforded. Unfortunately, however, increasing the amount of contrast media increases patient discomfort and increases the chances of adverse kidney complications as discussed above.

Another way of maximizing the diagnostic usefulness of the images acquired is to provide a number of imaging devices, or one large imaging device, that cover the entire field-of-view, each of which constantly acquire images so that stepping is not required. Unfortunately, such a scheme would dramatically increase (a) the patient's exposure to radiation and (b) the cost of the system.

Still another way of maximizing the diagnostic usefulness of the images acquired by the imaging device 110 is to extensively train medical personnel controlling the stepping of the imaging device 110/111 so that their judgment is improved. Unfortunately, angiographic imaging systems 100 are relatively expensive and thus, most medical facilities purchase only enough to meet their needs. Allocating training time decreases system throughput and, consequently, increases operating costs. Thus, needed training is difficult and costly to obtain.

Thus, a system which maximizes the diagnostic usefulness of angiographic images, using a judicious amount of contrast media, is needed. Such a system should permit off-line planning so that (a) an optimum volume of contrast media can be determined, (b) an optimum injection rate and/or pattern can be planned, (c) an optimum x-ray dose to which the patient will be exposed can be planned, and/or (d) optimum stepping times can be determined. Further, a system for training medical personnel to enhance their judgment as to stepping times is needed.

SUMMARY OF THE INVENTION

The present invention provides a method for determining when to step an x-ray angiography imaging device relative to a patient. This method is carried out by (a) receiving a mask image, (b) receiving a sequence of images; (c) extracting image features based on the received mask image and the received sequence of images, and (d) determining whether or not to step the imaging device relative to the patient based, at least in part, on the extracted image features. If it is determined to step the imaging device relative to the patient, the method is carried out by further (e) issuing a step command to means for stepping the imaging device relative to the patient, (f) moving the x-ray angiography imaging device relative to the patient, and (g) capturing a next frame of the image. If, on the other hand, it is determined not to step the imaging device relative to the patient, the method is carried out by further (e) capturing a next frame of the image.

In one version of the method of the present invention, the step of extracting image features may be carried out by (i) determining a DSA frame and/or a DIFF frame, (ii) determining features of the DSA frame and/or the DIFF frame, (iii) fitting the determined features of the DSA frame and/or the DIFF frame to a bolus propagation model function to generate fitted model parameters, and (iv) determining a bolus propagation state based on the fitted model parameters.

The DSA features may be determined by (i) enhancing pixels in the DSA frame so that pixels corresponding to relatively small and relatively large vessels have similar values, (ii) computing a vessel weight map based on the enhanced pixels, (iii) sectioning the DSA image into a predetermined number of regions, and (iv) for each region of the DSA image, (a) thresholding pixels of the vessel weight map to define a set of considered pixels, (b) multiplying values of the considered pixels by values of corresponding pixels of the DSA frame to form a set of products, (c) summing the set of products to form a first sum value, (d) summing the values of the considered pixels to form a second sum value, and (e) dividing the first sum value by the second sum value.

The DIFF features may be determined by (i) normalizing the DIFF frame, (ii) sectioning the DIFF image into a predetermined number of regions, and (iii) for each region of the DIFF image, (a) thresholding pixels of a vessel weight map to define a set of considered pixels, (b) multiplying values of the considered pixels by values of corresponding pixels of the DIFF frame to form a set of products, (c) summing the set of products to form a first sum value, (d) summing the considered pixel values to form a second sum value, and (e) dividing the first sum value by the second sum value.

In another version of the method of the present invention, the step of extracting image features may be carried out by (i) determining a DSA image, (ii) sectioning the DSA image into regions, (iii) in each of the regions of the DSA image, determining an average value of a predetermine percentage darkest pixels, (iv) determining a region of the DSA frame with a peak average value, (v) for each of the regions of the DSA frame, computing a change in its average value from a previous DSA frame, (vi) for each of the regions of the DSA frame, estimating a flow dynamics status based on the change in its average value, (vii) weighting the peak average value of the DSA frame based on the estimated flow dynamics status, and (viii) fitting the weighted peak average value of the DSA frame and that of the previous DSA frame to a function. The function may be a line fitting function. Further, the function may be extrapolated to predict a region with a peak average value in a future DSA frame.

In a third version of the method of the present invention, the step of extracting image features may be carried out by (i) computing a temporal sequence of DI arrays and/or a temporal sequence of DID arrays, (ii) generating ridge lines based the temporal sequence of DI arrays and/or the temporal sequence of the DID arrays, (iii) selecting those ridge lines with global maximum DI or DID values, and (iv) predicting a bolus location and/or a bolus speed, based on an emergence of the ridge lines with global maximum DI or DID values.

The ridge lines may be generated by (i) determining local points of local maxima DI or DID values in the temporal sequence of DI arrays and/or the temporal sequence of the DID arrays, and (ii) connecting corresponding local maxima points of temporally adjacent DI or DID arrays. Further, non-maxima values may be set to zero.

The present invention also provides a step determination unit for use with an imaging system including an imaging device, means for stepping the imaging device relative to a patient, and a contrast media injection means. The step determination unit includes (a) an input for receiving images from the imaging device, (b) means for extracting features from images received at the input to generate extracted features, (c) means for determining when to issue a step command based on the extracted features, and (d) an output for providing a step command to the means for stepping the imaging device based on when the means for determining determines to issue a step command.

The means for determining when to issue a step command may base its determination on (a) a user input, (b) a present station of the imaging device, (c) a predicted bolus rate of contrast media injected by the means for injecting, (d) a predicted bolus location of the contrast media, (e) a bolus length of the contrast media, (f) a leg area being tracked, (g) a vessel area being tracked, (h) a step delay, (i) a screen overlap, (j) an operator step preference, and/or (k) a step function selection. The means for determining may include (i) means for determining a DSA frame and/or a DIFF frame, (ii) means for determining features of the DSA frame and/or the DIFF frame, (iii) means for fitting the determined features of the DSA frame and/or the DIFF frame to a predetermined bolus model function to generate a fitted model, and (iv) means for determining a bolus propagation state based on the fitted model and another fitted model.

The means for determining DSA features may include (i) means for enhancing pixels in the DSA frame so that pixels corresponding to relatively small and relatively large vessels have similar values, (ii) means for computing a vessel weight map based on the enhanced pixels, (iii) means for sectioning the DSA image into a predetermined number of regions, (iv) means for, in each region of the DSA image, thresholding pixels of the vessel weight map to define a set of considered pixels, (v) means for, in each region of the DSA image, multiplying values of the considered pixels by values of corresponding pixels of the DSA frame to form a set of products, (vi) means for, in each region of the DSA image, summing the set of products to form a first sum value, (vii) means for, in each region of the DSA image, summing the values of the considered pixels to form a second sum value, and (viii) means for, in each region of the DSA image, dividing the first sum value by the second sum value.

The means for determining DIFF features may include (i) means for normalizing the DIFF frame, (ii) means for sectioning the DIFF image into a predetermined number of regions, and (iii) means for, in each region of the DIFF image, thresholding pixels of a vessel weight map to define a set of considered pixels, (iv) means for, in each region of the DIFF image, multiplying values of the considered pixels by values of corresponding pixels of the DIFF frame to form a set of products, (v) means for, in each region of the DIFF image, summing the set of products to form a first sum value, (vi) means for, in each region of the DIFF image, summing values of the considered pixels to form a second sum value, and (vii) means for, in each region of the DIFF image, dividing the first sum value by the second sum value.

The means for extracting image features may include (i) means for determining a DSA image, (ii) means for sectioning the DSA image into horizontal regions (iii) means for, in each of the regions of the DSA image, determining an average value of a predetermine percentage darkest pixels, (iv) means for determining a region of the DSA frame with a peak average value, (v) means for, in each of the regions of the DSA frame, computing a change in its average value from a previous DSA frame, (vi) means for, in each of the regions of the DSA frame, estimating a flow dynamics status based on the change in average value, (vii) means for weighting the peak average value of the DSA frame based on the estimated flow dynamics status, and (viii) means for fitting the weighted peak average value of the DSA frame and that of the previous DSA frame to a function. The function may be a line fitting function. Further, the function may be extrapolated to predict a region with a peak average value in a future DSA frame.

In another embodiment of the device of the present invention, the means for extracting image features may include (i) means for computing a temporal sequence of DI arrays and/or a temporal sequence of DID arrays, (ii) means for generating ridge lines based the temporal sequence of DI arrays and/or the temporal sequence of the DID arrays, (iii) means for selecting those ridge lines with global maximum DI or DID values, and (iv) means for predicting a bolus location and/or a bolus speed, based on an emergence of the ridge lines with global maximum DI or DID values.

The means for generating ridge lines may include (i) means for determining local points of local maxima DI or DID values in the temporal sequence of DI arrays and/or the temporal sequence of the DID arrays, and (ii) means for connecting corresponding local maxima points of temporally adjacent DI or DID arrays. The step determination unit may further include means for setting non-maxima values to zero.

The present invention also provides a visualization aid for use with an imaging system including an imaging device, means for stepping the imaging device relative to a patient, and a contrast media injection means. The visualization aid includes (i) an input for receiving images from the imaging device, (ii) means for extracting features from images received at the input to generate extracted features, (iii) means for determining a video output based on the extracted features, and (iv) an output for providing the video output. The video output may be based on (a) a user input, (b) a present station of the imaging device, (c) a predicted bolus rate of contrast media injected by the means for injecting, (d) a predicted bolus location of the contrast media, (e) a bolus length of the contrast media, (f) a leg area being tracked, (g) a vessel area being tracked, (h) a step delay, (i) a screen overlap, (j) an operator step preference, and/or (k) a step function selection. Alternatively, the video output may be based on the estimated flow dynamics status of each region.

The means for extracting features may include (i) means for determining a DSA image, (ii) means for sectioning the DSA image into horizontal regions, (iii) means for, in each of the regions of the DSA image, determining an average value of a predetermine percentage darkest pixels, (iv) means for determining a region of the DSA frame with a peak average value, (v) means for, in each of the regions of the DSA frame, computing a change in its average value from a previous DSA frame, (vi) means for, in each of the regions of the DSA frame, estimating a flow dynamics status based on the change in average value, (vii) means for weighting the peak average value of the DSA frame based on the estimated flow dynamics status, and (viii) means for fitting the weighted peak average value of the DSA frame and that of the previous DSA frame to a function. The function may be a line fitting function.

The visualization aid of may further include means for generating data for displaying DSA features and/or means for generating data for displaying DIFF features.

The estimated flow dynamics statuses may include (a) "wash-in", (b) "approaching maximum opacity", (c) "passing maximum opacity", and (d) "wash-out". In this case, the video output provides a distinct color for each of the estimated flow dynamics statuses.

BRIEF DESCRIPTION OF THE DRAWINGS

FIG. 11b is a flow diagram of a ridge line generation process which may be used by the feature extraction process of FIG. 11a.

FIG. 14a is a plot of a value DI(y,t) which may be used in the third feature extraction process of FIG. 11a.

FIG. 14b is a plot of a value DID(y,t) which may be used in the third feature extraction process of FIG. 11a.

FIG. 16a is a plot of "ridge lines" of DI(y,t) which may be used by the third feature extraction process of FIG. 11a.

FIG. 16b is a plot of "ridge lines" of DID(y,t) which may be used by the third feature extraction process of FIG. 11a.

DETAILED DESCRIPTION OF THE INVENTION

The present invention concerns novel methods and apparatus for controlling the image acquisition of an x-ray angiography imaging device, for training medical professionals to operate an imaging device, and for providing a visualization aid to a medical professional operating an imaging device. The following description is presented to enable one skilled in the art to make and use the invention, and is provided in the context of a particular application and its requirements. Various modifications to the preferred embodiment will be apparent to those skilled in the art, and the general principles set forth below may be applied to other embodiments and applications. Thus, the present invention is not intended to be limited to the embodiment shown.

Throughout this description; a "mask image" is an x-ray image of the patient before a contrast medium is injected. A "DSA" (or digital subtraction angiographic) image is a difference between a mask image and a captured contrast image. A "DIFF" (or difference) image is determined based on the difference between any two captured contrast images. Forming DSA and DIFF images is known in the art. Unless stated otherwise, in the specification, a DIFF image in the described exemplary embodiments will be determined based on the difference between two temporally adjacent images.

In the following, the functions performed by the present invention will first be described. Then, the structure of an exemplary embodiment and methodologies for practicing the present invention will be described. Thereafter, an example of the operation of the present invention will be described.

The methods and apparatus of the present invention maximize the diagnostic and/or therapeutic usefulness of angiographic images, while minimizing contrast media and x-ray doses to a patient, by automating a step determination process and/or by providing a visualization aid to a medical professional operating an x-ray angiographic system. The time to step is determined based on, inter alia, features of past and current angiographic images. Methods and apparatus of the present invention also provide a simulation tool for training medical personnel to command a step of an imaging device at a proper time.

Figure 1A:
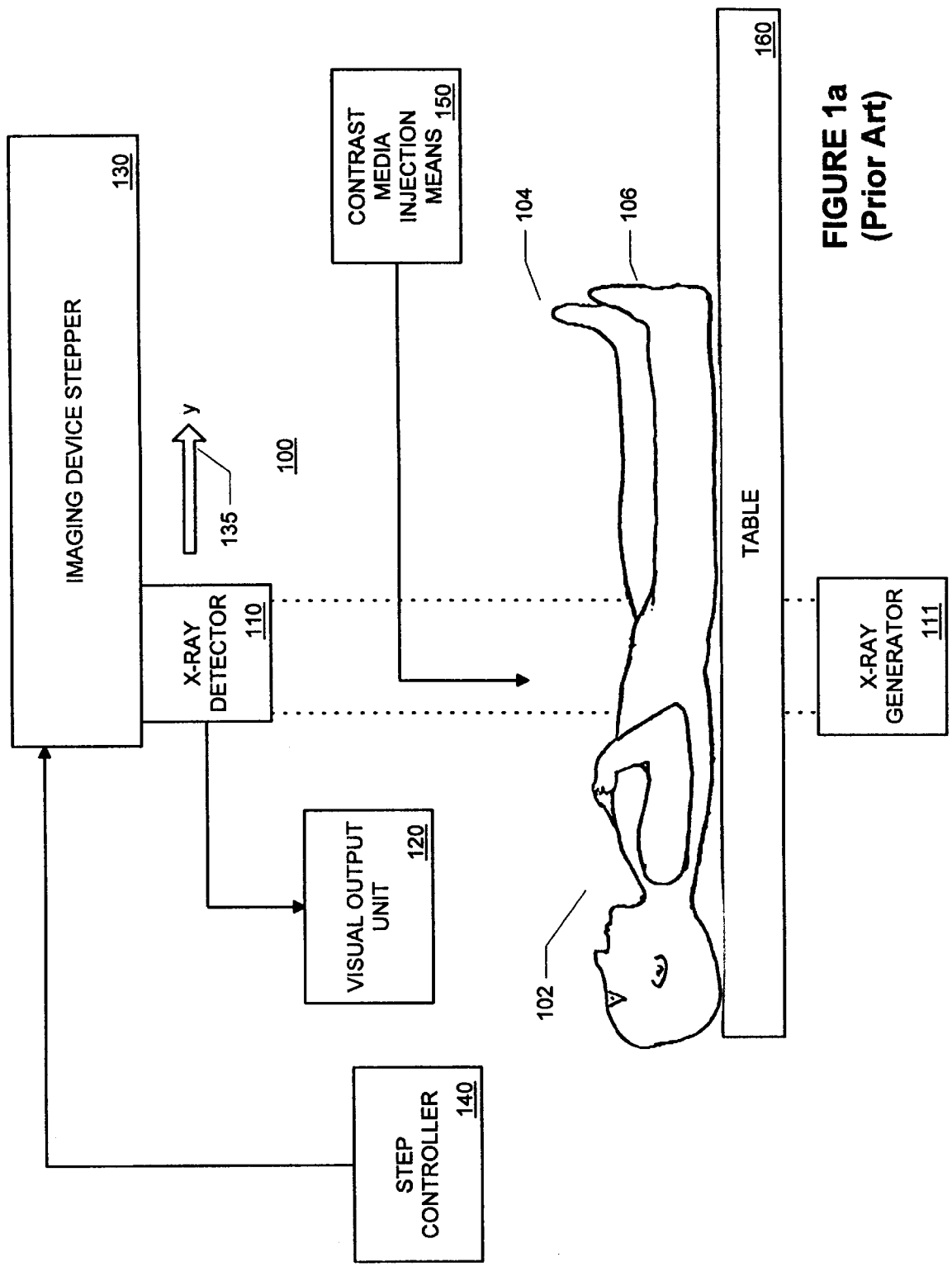
FIG. 1a is a high level block diagram of a conventional angiographic system.
Figure 1B:
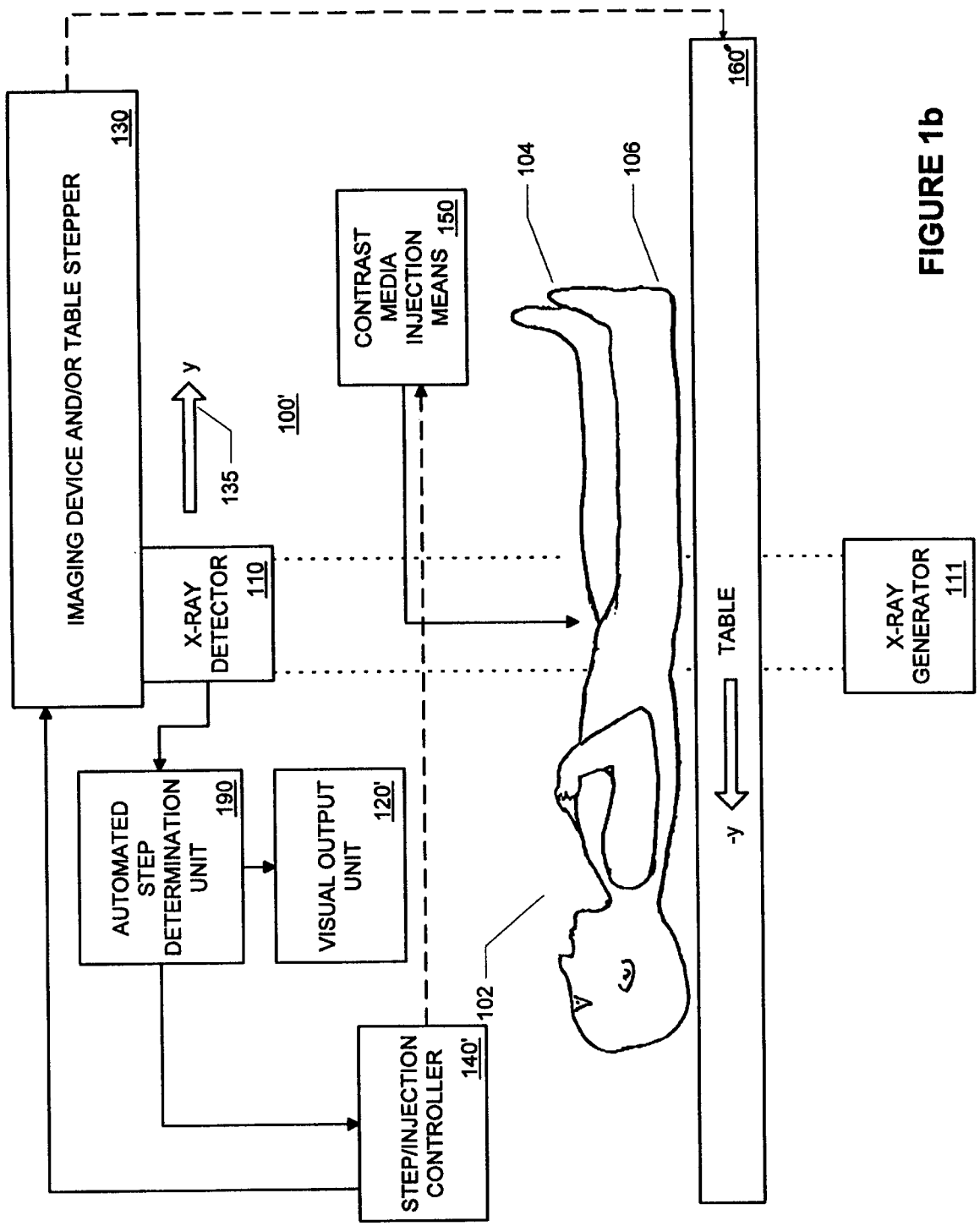
FIG. 1b is a high level block diagram of an angiographic system which embodies the present invention.

FIG. 1b is a high level block diagram of a system 100' for maximizing the diagnostic usefulness of angiographic images to be acquired by the x-ray detector 110 of an imaging device 110/111. The system 100' embodies the present invention. Basically, the contrast media injection means 150, the imaging device 110/111 and the image device and/or table stepper 130 may be the same as those shown in the known system 100 of FIG. 1a. An automated step determination unit (and/or visualization aid unit) 190 is provided, the structure and operation of which is discussed below. The automated step determination unit 190 receives image information from the x-ray detector 110 of the imaging device 110/111 and provides outputs to the visual output unit 120' and the step/injection controller 140'. The visual output unit 120' is basically the same at that 120 of the known system 100 of FIG. 1a but receives its input from the automated step determination unit 190 rather than directly from the x-ray detector 110 of the imaging device 110/111.

Figure 20A:
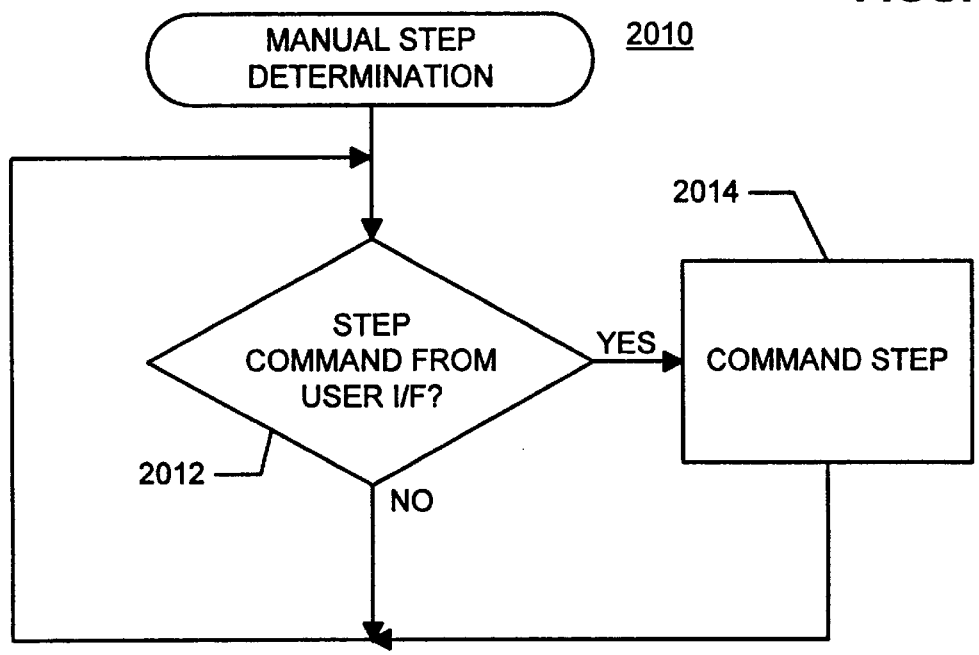
FIGS. 20a–20d are flow diagrams of various modes of a step determination process used in methods of the present invention.
Figure 20B:
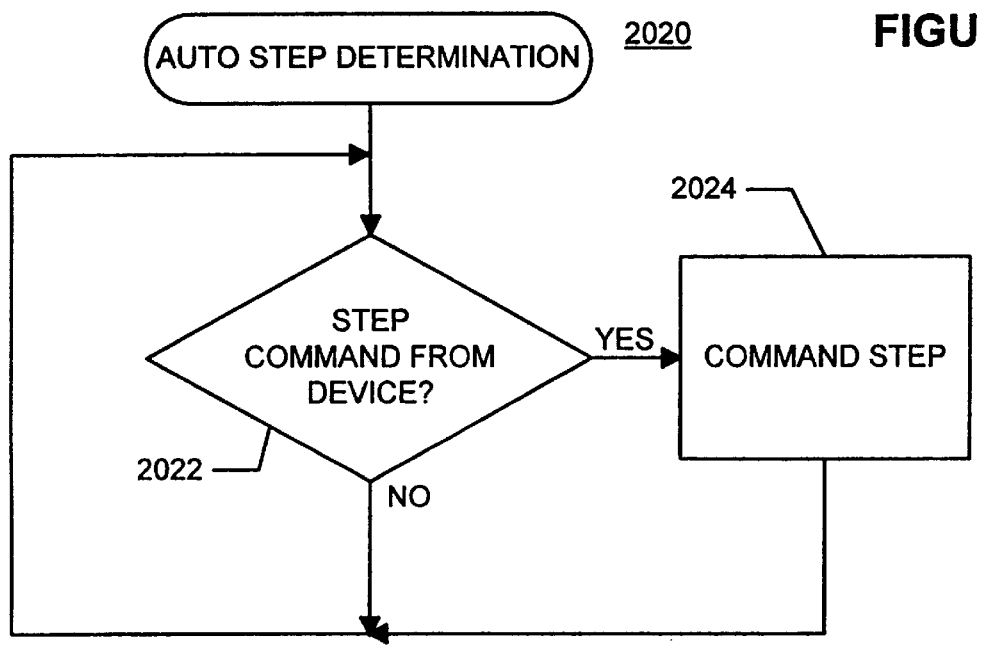
Figure 20C:
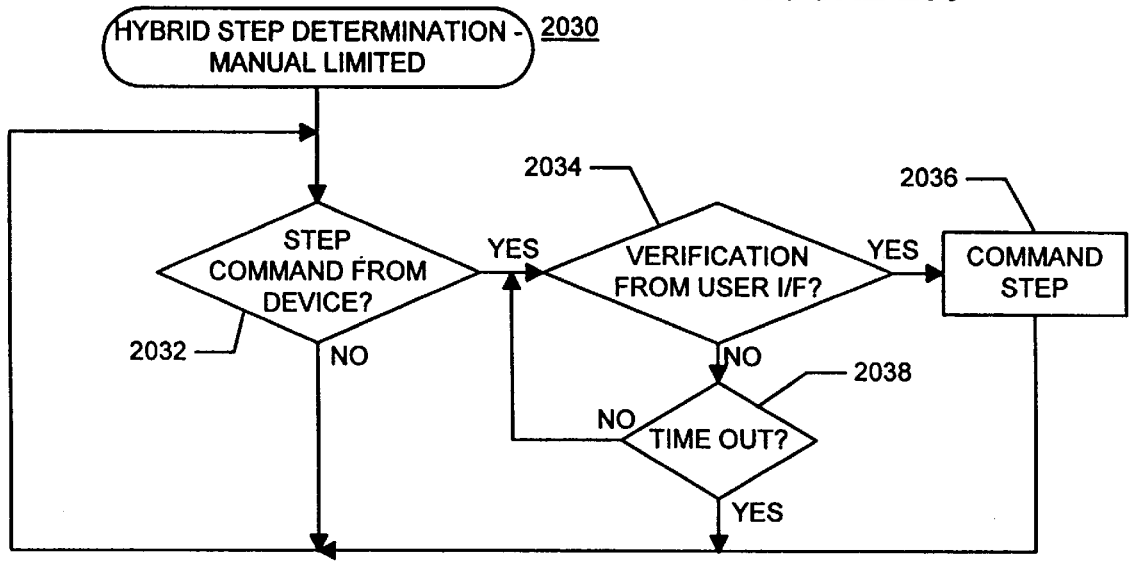
Figure 20D:
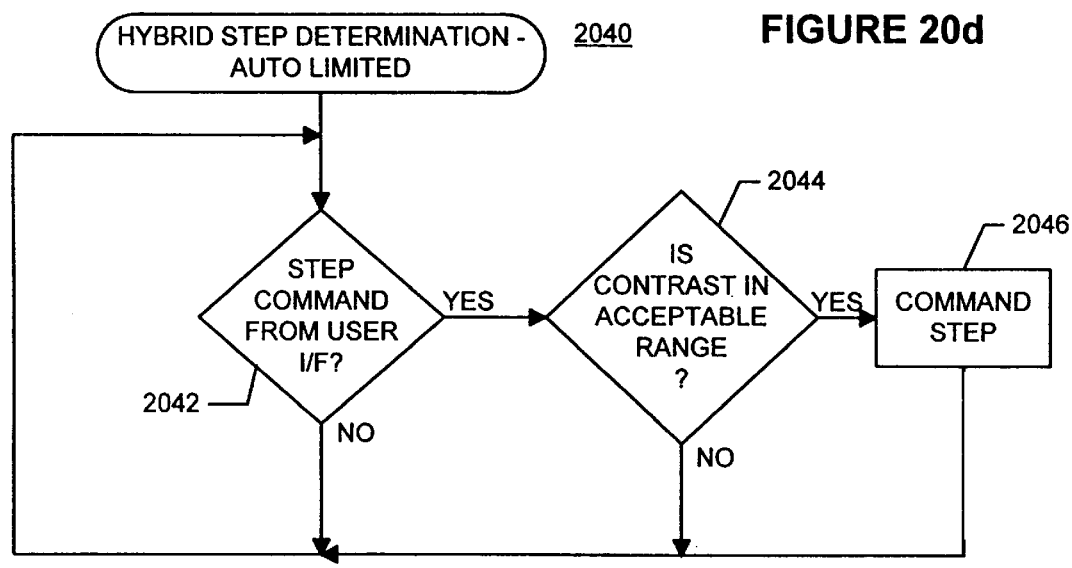

Referring to FIGS. 20a through 20d, the step/injection controller 140' may control the imaging device stepper 130 based on an input from the automated step determination unit 190 in a auto mode (see, e.g., FIG. 20b), an input from a medical professional in a manual mode (see, e.g., FIG. 20a), or inputs from both the step determination unit 190 and the medical professional in a hybrid manual-auto mode (see, e.g., FIGS. 20c and 20d). FIG. 20a is a flow diagram of an exemplary manual step determination process 2010. As shown in steps 2012 and 2014, if a step command is received from the user interface (see, e.g., process 350 of FIG. 3), a step command is issued to the image device and/or table stepper 130. FIG. 20b is a flow diagram of an exemplary auto step determination process 2020. As shown in steps 2022 and 2024, if a step command is received from the automated step determination unit 190, a step command is issued to the imaging device and/or table stepper 130.

In the hybrid manual-auto mode, the input of the medical professional, under constraints of inputs of the automated step determination unit 190, may control the stepping of the imaging device 110/111 (see, e.g., FIG. 20d) or the input of the automated step determination unit 190, under constraints of the inputs of the medical professional, may control the stepping of the imaging device 110/111 (see, e.g., FIG. 20c). FIG. 20c is a flow diagram of an exemplary process 2030 for performing a hybrid step determination in which an automatically generated step command is limited by a manual input. As shown in steps 2032, 2034, 2038, and 2036, when a step command is generated by the automated step determination unit 190, the operator must verify the step within a predetermined time-out period. If the operator verifies the step within the time-out period, a step command is issued to the imaging device and/or table stepper 130. If, on the other hand, the user fails to verify the step within the time-out period, no step command is issued. Finally, FIG. 20d is a flow diagram of an exemplary process 2040 for performing a hybrid step determination in which a manually entered step command is limited. As shown in steps 2042, 2044, and 2046, if a step command is received from the user interface, and if the automated step determination unit 190 determines that the contrast medium is within an acceptable range, a step command is issued to the imaging device and/or table stepper 130.

The step/injection controller 140' may also be used to control the contrast media injection means 150 as shown by the dashed line.

In alternative embodiments, the table 160' may be moved in the -y direction with respect to the imaging device 110/111 or both may be moved with respect to one another. Thus, the imaging device and/or table stepper 130 may provide a step command signal to a movable table 160 as shown by the dashed lines. Accordingly, stepping the imaging device 110/111 relative to the patient 102 should be broadly interpreted to mean (a) moving the imaging device 110/111, (b) moving the table 160, or (c) moving both the imaging device 110/111 and the table 160.

Figure 2:
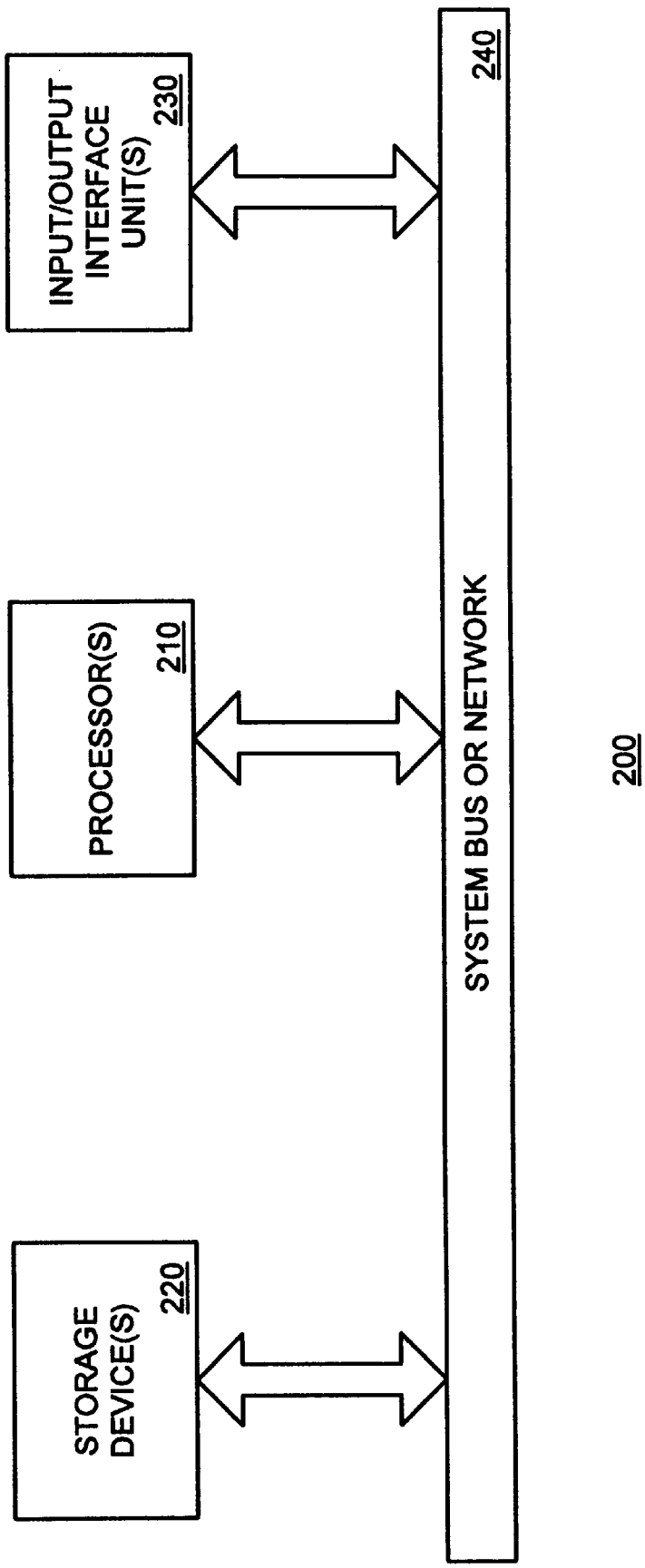
FIG. 2 is a high level block diagram of an apparatus which embodies the present invention.

FIG. 2 is a high level block diagram of a system 200 which may be used to implement the automated step determination unit (and/or visualization aid unit) 190 (and step controller 140). The system 200 includes at least one processor (e.g., a microprocessor, an ASIC, or specialized hardware or firmware) 210, at least one storage device 220, and at least one input/output interface unit 230, each of which may share a system bus (or which may communicate via network) 240. The processor(s) 210 executes instructions, which may be stored in the storage device(s) 230 or which may be received via the input/output interface unit(s) 230, to effect the processes discussed below. The input/output interface unit(s) 230 accepts image information from the imaging device 110, conditions output for communication to the visual output device 120', and conditions output for communication to the step controller 140'.

Figure 3:
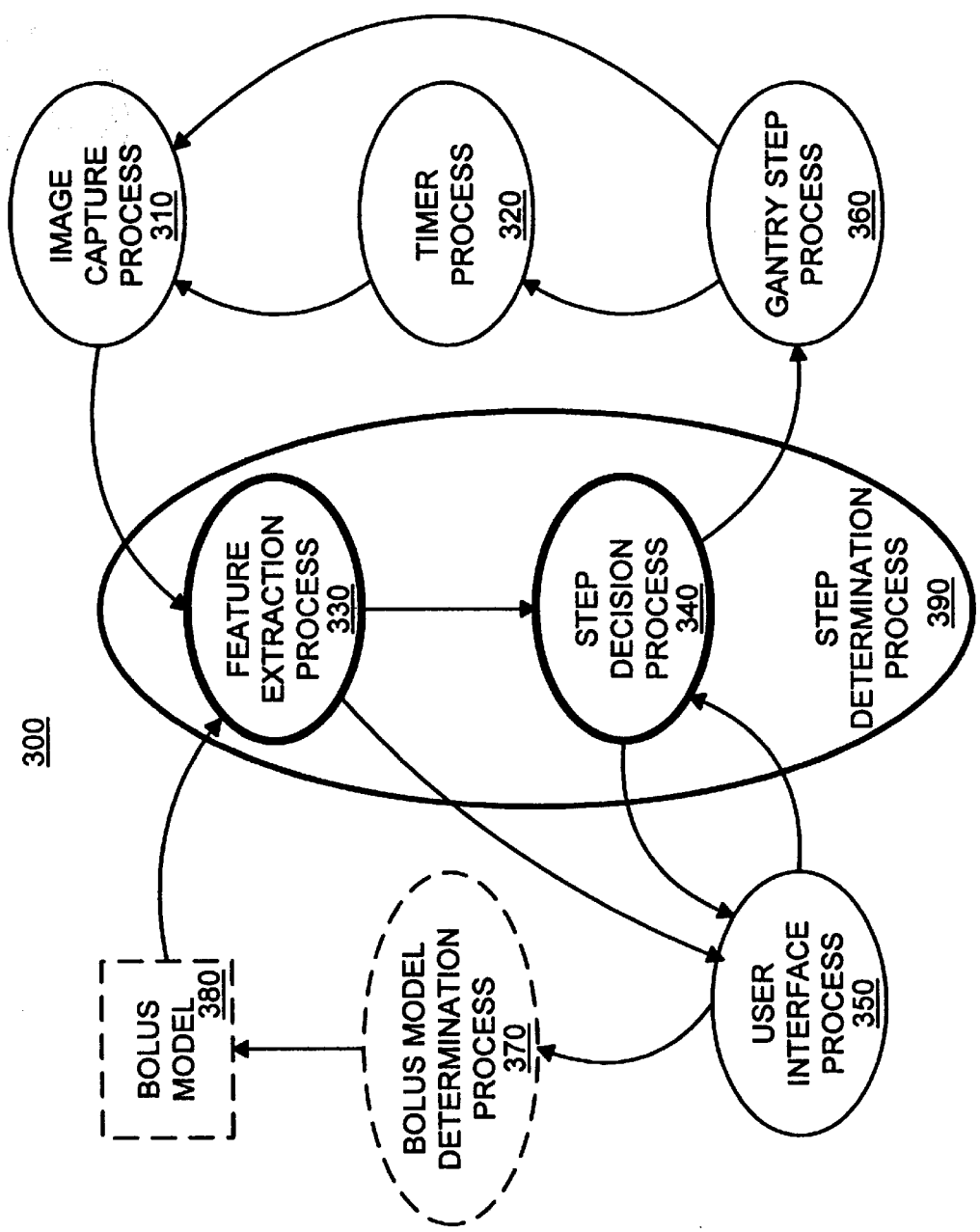
FIG. 3 is a bubble diagram of processes of the present invention.

FIG. 3 is a process bubble diagram of a process 300 for effecting the present invention. The image capture process 310, which may be carried out by the x-ray detector 110 of the imaging device 110/111, may capture images of a patient by known angiographic techniques. The time at which the imaging capture process 310 acquires such images is based on input from a timer process 320 and a gantry (and/or table) step process 360. More specifically, the image capture process 310 acquires images periodically, but typically not when the imaging device 110/111 is being stepped from one position to a next position.

Images acquired at the image capture process 310 carried out on the imaging device 110/111 are provided to a feature extraction process 330. The feature extraction process 330 may be carried out by a processor(s) 210, (or special hardware or firmware) executing appropriate instructions. The feature extraction process 330 will provide information to a step decision process 340. The step decision process 330 may also be carried out by a processor(s) 210 executing appropriate instructions. The step decision process 330 may also receive information from a user interface process 350.

Based on the information received from the feature extraction process 330 and/or the user interface process 350 (as discussed above with reference to FIGS. 20a–20d), the step decision process 340 provides stepping commands to the gantry (and/or table) step process 360. The step decision process 340 may be replaced by, or supplemented with, a visualization aid process. The gantry (and/or table) step process 360 may be carried out by the image device stepper 130. As will be discussed below, a bolus model function 380 may be used by a particular feature extraction process 330. In such an embodiment, the bolus model function 380 is generated by a bolus determination process 370. The processes relevant to understanding and practicing the present invention will be discussed below.

Figure 4:
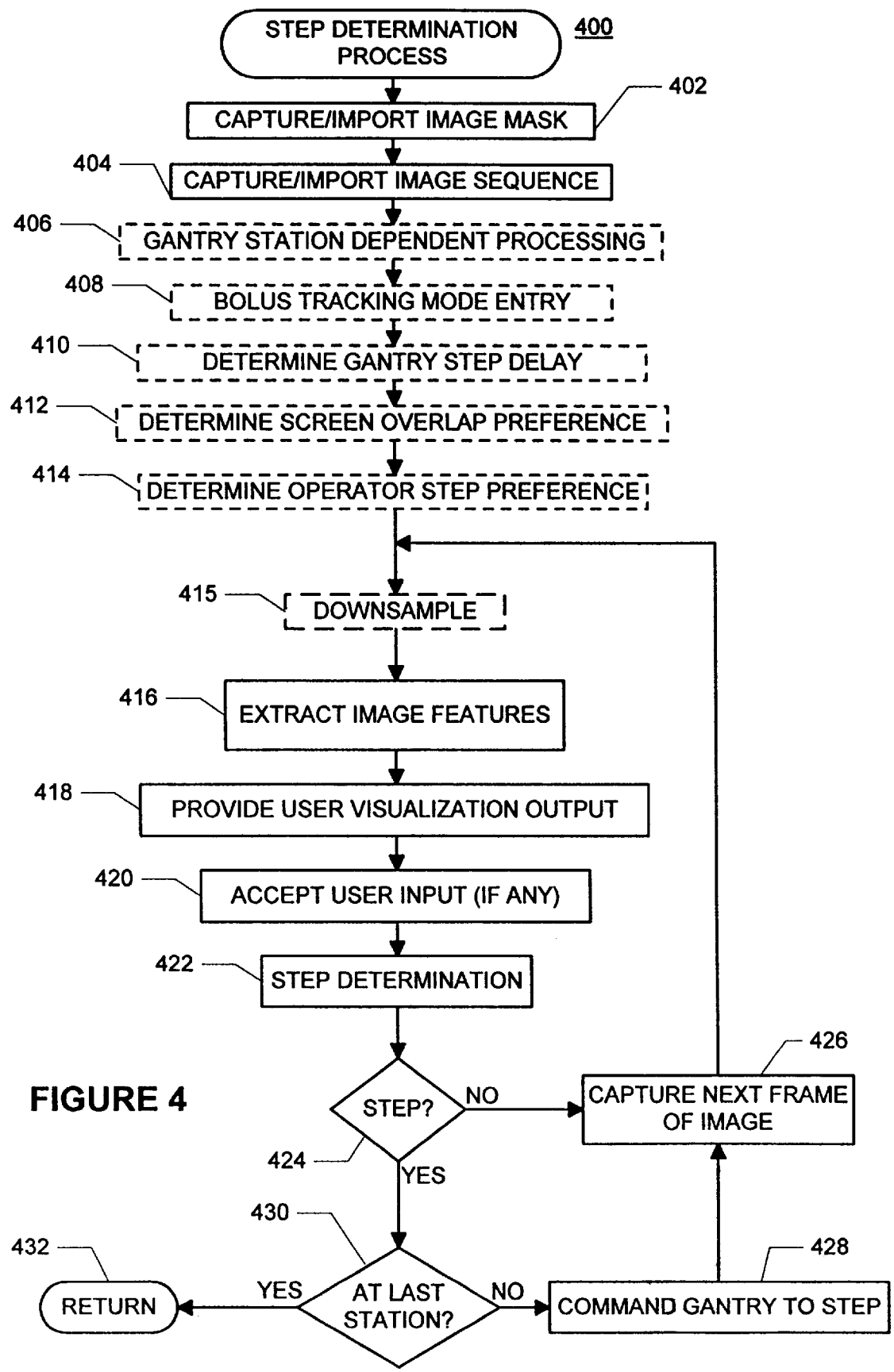
FIG. 4 is a high level flow diagram of a method of the present invention.

First, a flow diagram of a step determination process 400, which includes both a feature extraction process 330 and the step decision process 340, is shown in FIG. 4. Starting at step 402, an image mask is imported or captured. Referring to FIG. 1b, the imaging device 110/111 captures images of the patient 102 before the contrast media is injected. These images are known as mask images. Thereafter, as shown in step 404, after the contrast media has been injected, a first image or frames of a first image sequence are captured. This step 404 is carried out by the imaging device 110/111 based on timing signals from the timer process 320.

Figure 5:
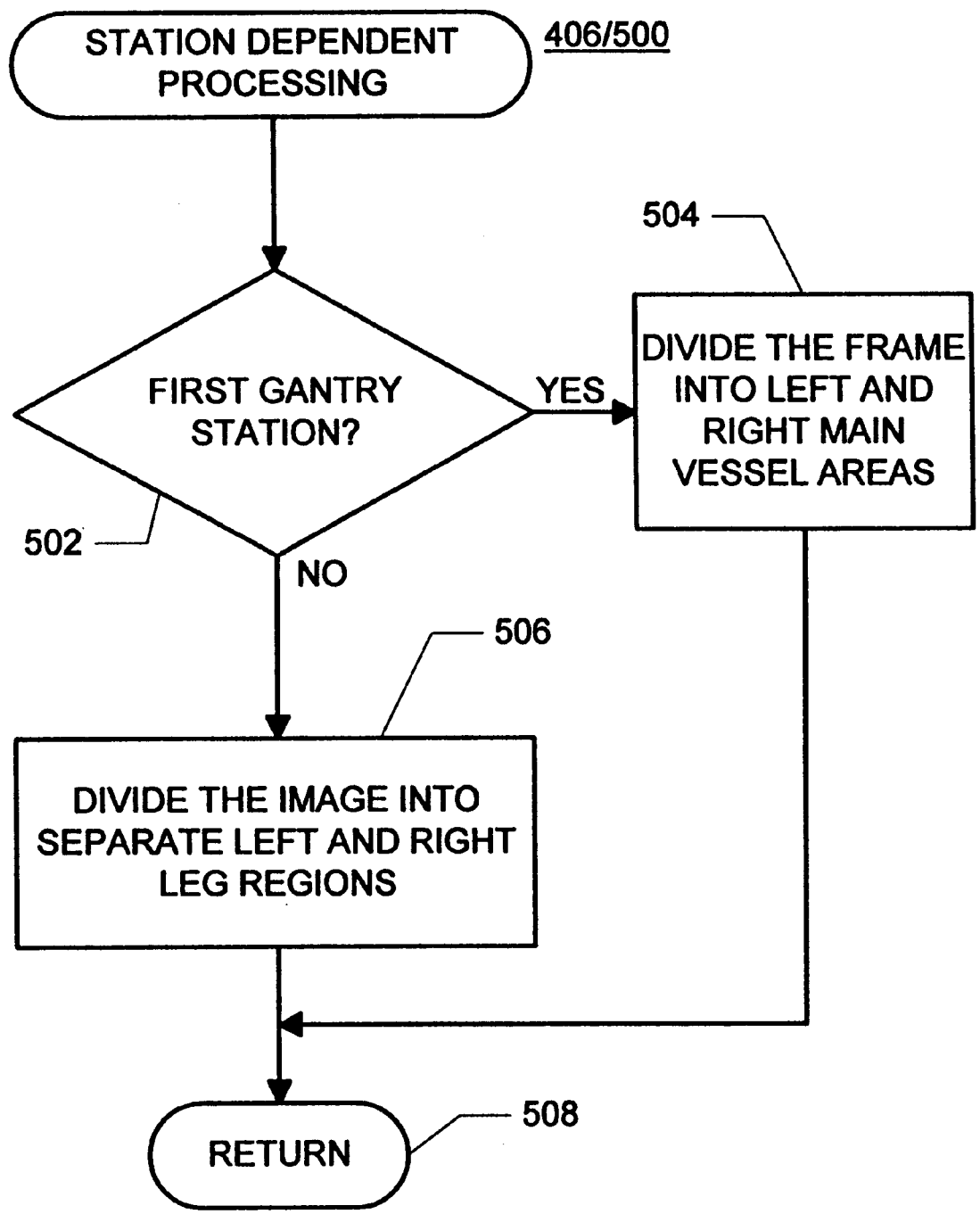
FIG. 5 is a flow diagram of station dependent processing of a method of the present invention.

In optional step 406, shown in dashed lines, gantry station dependent processing 406 takes place. Referring to FIG. 5, which is a flow diagram of the station dependent processing 406/500, if, as shown in step 502, the imaging device 110 is at a first station, then, as shown in step 504, the frame of the image is divided into left and right main vessel areas. Referring briefly to user interface display 1800 of FIG. 18, this step may be carried out because when the imaging device 110/111 is at its first station, images 1850 of the patient's hip and groin area are captured. Processing then continues at return node 508. If, on the other hand, as shown in steps 502 and 506, the imaging device 110 is not at the first gantry station, then the images acquired are divided into separate left and right leg regions. Processing then continues at return node 508. The present gantry station may be a factor used by the step decision process 340.

Figure 6:
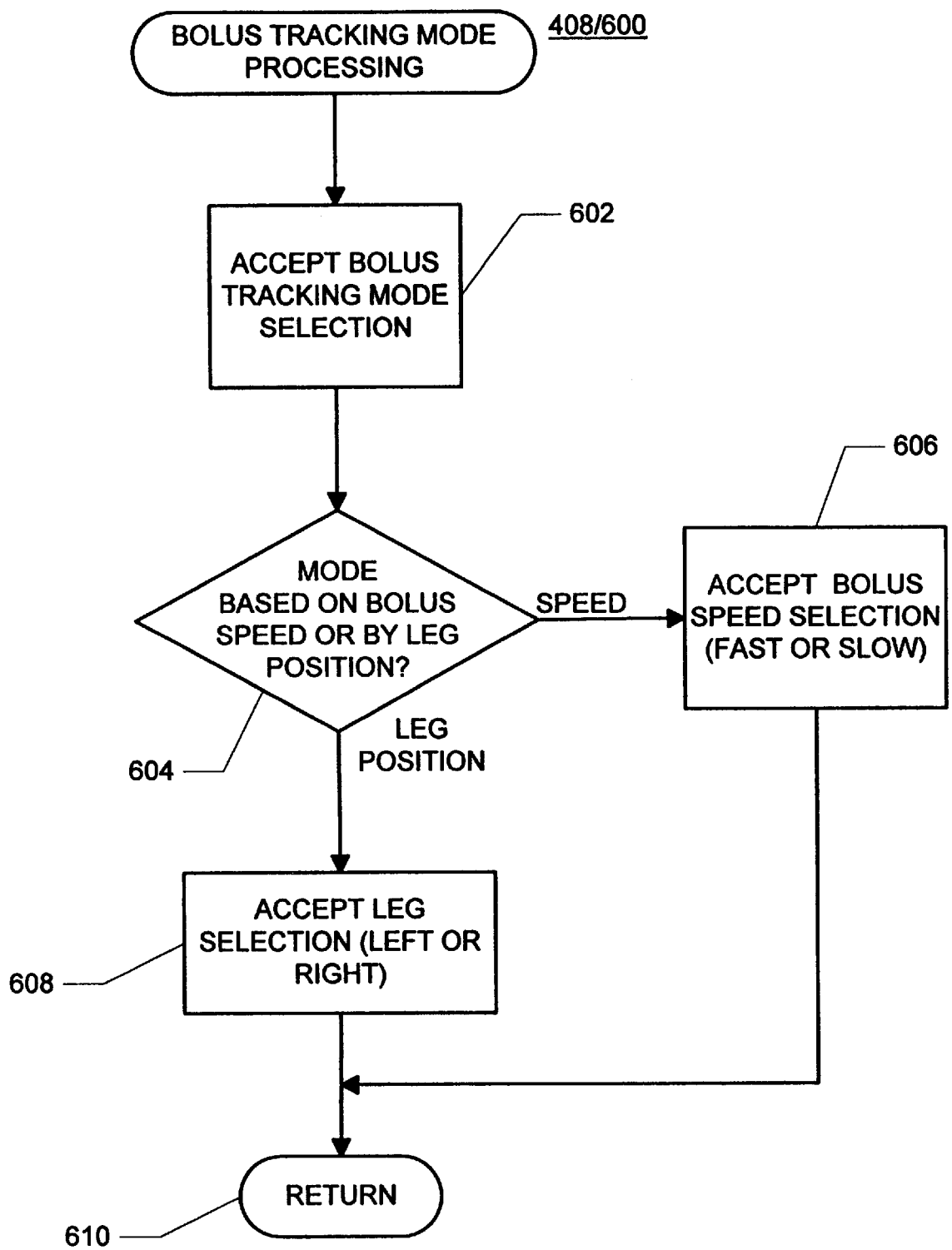
FIG. 6 is a flow diagram of bolus tracking mode processing of a method of the present invention.

In optional step 408, shown in dashed lines, a bolus tracking mode entry takes place. The bolus tracking mode may be a factor used by the step decision process 340. Referring to FIG. 6, which is a flow diagram of the bolus tracking mode processing 408/600, as shown in step 602, a bolus tracking mode, either based on bolus speed or based on a leg, selection is accepted. This selection may be made via the user interface process 350. If, as shown in steps 604 and 606, the bolus tracking mode selected is based on bolus speed, a bolus speed is accepted and processing continues at return node 610. If, on the other hand, as shown in steps 604 and 608, the bolus tracking mode selected is based on a leg, the leg selection (left or right) is accepted and processing continues at return node 610. The bolus tracking mode may be a factor used by the step decision process 340.

In optional step 410, shown in dashed lines, a gantry (and/or table) step delay may be determined. This predetermined delay may be manually entered or based on gantry station (and/or table) identification information which allows the look-up of such delay information. The gantry (and/or table) step delay information may be a factor used by the step decision process 340.

In optional step 412, shown in dashed lines, a screen overlap preference may be determined. In particular, an angiographer may provide an amount of screen overlap that they feel comfortable with. Such screen overlap preferences, if any, may be entered by the angiographer before the angiographic process. The angiographer's screen overlap preference may be a factor used by the step decision process 340.

In optional step 414, shown in dashed lines, an angiographer step preference may be determined. In particular, different angiographers or different analysts may prefer to step the gantry (and/or table) at the leading edge of the bolus or slightly before or after the leading edge of the bolus. Such step preferences, if any, may be entered by the angiographer before the angiographic procedure begins. The step preference may be a factor used by the step decision process 340.

Down sampling step 415 is shown in dashed lines since it is an optional step. Downsampling reduces the amount of data of an image to the extent needed to permit real-time operation of the present invention. For example, if the images (e.g., mask image and sequence of images) captured by the x-ray detector 110 of the imaging device 110/111 are 1024 pixels by 1024 pixels, they may be downsampled to 256 pixels by 256 pixels to speed processing. Naturally, as processing becomes faster, this downsampling step 415 may no longer be required.

Thereafter, features are extracted from the images as shown in step 416. Three (3) exemplary feature extraction techniques are discussed in detail below. In addition, a visualization aid output may be provided to an operator as shown in step 418. This visualization aid output may be provided on the visual output unit 120' under control of the user interface process 350. As shown in step 420, operator input, if any, may be accepted. This step may be effected by the user interface process 350. The operator input may be a factor used by the step decision process 340.

Based on the extracted features, other step determination factors discussed above, and/or the operator input (see, e.g., FIGS. 20a through 20d discussed above), a step determination process is performed as shown in step 422. If, as shown in steps 424 and 426, it is determined not to step, the next frame of the image sequence is captured and the processing is repeated at step 415. If, on the other hand, as shown in steps 424, 430, 428 and 426, it is determined to step and the imaging device 110 is not at the last station, a step command is sent to the image device (and/or table) stepper (or gantry) 130, a first frame of an image at a next station is captured, and processing continues at step 415. If, as shown in steps 424, 430 and 432, it is determined to step and the imaging device 110/111 is at the last station, the step determination process 400 ends and processing continues at return node 432.

As discussed above with reference to the image feature extraction step 416 of FIG. 4, three (3) exemplary techniques for extracting features from the images are described here; feature extraction may be performed by (i) fitting the image data to a bolus model function, (ii) generating a linear fit of peak image data, or (iii) analyzing directional topographic data. Each of these techniques will now be described.

A feature extraction technique which fits image data to a bolus model function is described with reference to FIG. 7. As is known, a bolus model function may be generated by convoluting a simple bolus function, a Gaussian distribution function, a delay function, and an exponential function. The simple bolus function includes an initial, linearly increasing region followed by a plateau region which is followed by a linearly decreasing region.

Figure 7:
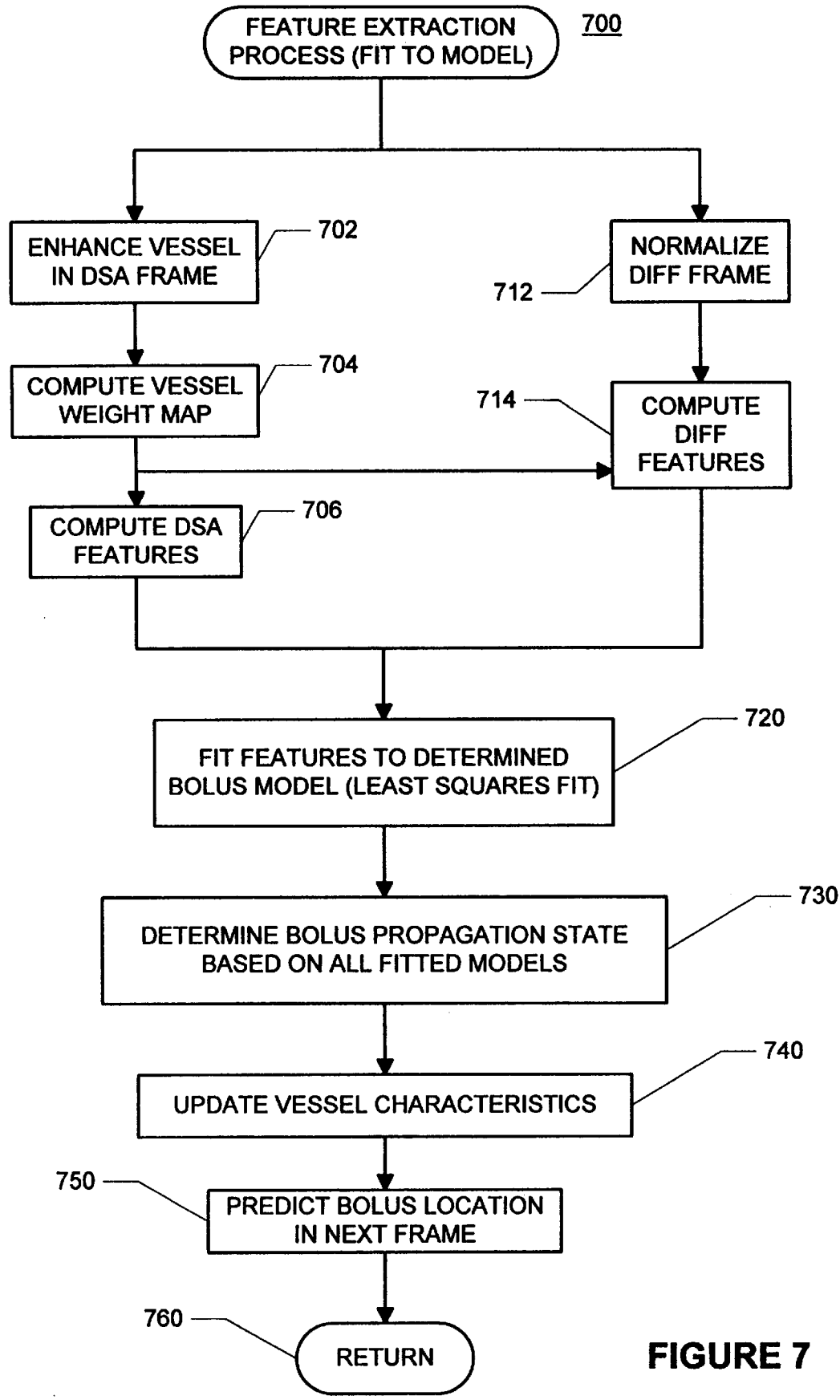
FIG. 7 is a flow diagram of a first embodiment of a feature extraction process of a method of the present invention.

Referring now to FIG. 7, which is a flow diagram of a feature extraction technique 700 which fits image data to a bolus model, a generated DSA image frame may be preprocessed, in steps 702, 704, and 706, to find pixels which belong to a vessel. First, as shown in step 702, vessels in the DSA frame are enhanced so that smaller vessels have the same or similar pixel values as those of larger vessels while maintaining a low pixel value for non-vessel background portions of the image. An example of such a vessel enhancement process is described in U.S. patent application Ser. No. 08/796,331, entitled "Multi-Scale Adaptive System for Enhancement of an Image in X-Ray Angiography," filed on Feb. 7, 1997 (incorporated herein by reference). Next, as shown in step 704, a vessel weight map is computed. Basically, after the vessel enhancement of step 702, the pixels of the resulting image will tend to have either large negative values or values close to zero. The large negative values are converted to approximately one and the zero values are converted to approximately zero. More specifically, in the vessel weight map, each weighted pixel value ($W_p$) may be defined as:

$$W_p = 1 - e^{\left(\frac{\text{enhanced pixel value}_p}{N}\right)} \quad (1)$$

where N a normalization scale of the enhanced DSA frame.

P=pixel index.

A normalization scale of the enhanced DSA frame can be determined, for example, by the following equation:

$$N \equiv \frac{\sum_{i \in \text{all pixels}} \text{enhanced pixel value}_i}{\text{Number of pixels}} \cdot K \quad (2)$$

where K is a constant.

Finally, as shown in step 706 DSA features are computed. More specifically, the DSA image may be divided into a number of left regions and a number of right regions. For each region of the DSA image, the following steps are performed. First, the vessel weight map is thresholded so that only pixels of the vessel weight map greater than a predetermined threshold value are considered. Next, a weighted average vessel intensity is determined. The weighted average vessel intensity value is determined by (i) multiplying the weighted pixel values to be considered (i.e., those greater that the predetermined threshold) by the values of corresponding pixels of the DSA image, (ii) summing the resulting products to generate a first sum value, (iii) summing the weighted pixel values to be considered to generate a second sum value, and (iv) dividing the first sum value by the second sum value. In other words, the weighted average vessel intensity (AVI) value may be determined by the following equation:

$$AVI = \frac{\sum_{i \in \text{all considered pixels}} \text{weighted pixel}_i * DSA \text{ pixel value}_i}{\sum_{i \in \text{all considered pixels}} \text{weighted pixel}_i} \quad (3)$$

Referring now to the step 712 of normalizing the DIFF frame, one way of normalizing the DIFF frame is simply to divide the DIFF pixel values by the DSA pixel values to obtain a percent difference rather than an absolute difference. The problem with such an approach is that very small DSA pixel values may cause the normalized DIFF pixel values to become too large. Accordingly, for each of the predefined regions of the DIFF frame, the DIFF pixel values are processed as follows. First, if the magnitude (or absolute value) of the DIFF pixel value is greater than the magnitude (or absolute value) of the DSA-weight product, then the DSA-weight product is substituted for the value of the DIFF pixel to generate a modified DIFF frame. Next, the resulting pixel values of the modified DIFF frame are multiplied by the weight value. This step helps to eliminate background noise. Finally, the result is divided by the DSA values. A normalized DIFF frame results which, in contrast to the simple normalization calculation, will not have very large values for pixels corresponding to DSA pixels having a very small magnitude.

Next, as shown in step 714, DIFF features are determined. This step 714 is performed in a similar manner to the step of computing DSA features 706 discussed above. More specifically, for each region of the normalized DIFF image, the following steps are performed. First, the vessel weight map is thresholded so that only pixels of the vessel weight map greater than a predetermined threshold value are considered. Next, a weighted average of the normalized DIFF image is determined. The weighted average normalized DIFF value is determined by (i) multiplying the weighted pixel values to be considered (i.e., those greater that the predetermined threshold) by the values of corresponding pixels of the normalized DIFF image, (ii) summing the resulting products to generate a first sum value, (iii) summing the weighted pixel values to be considered to generate a second sum value, and (iv) dividing the first sum value by the second sum value. In other words, the weighted normalized DIFF value ("WNDIFF") may be determined by the following equation:

$$WNDIFF = \frac{\sum_{i \in \text{ all considered pixels}} \text{weighted pixel}_i * \text{Normalized } DIFF \text{ pixel value}_i}{\sum_{i \in \text{ all considered pixels}} \text{weighted pixel}_i} \quad (4)$$

Thereafter, as shown in step 720, the DSA and DIFF features are fit, using a least square fit procedure for example, to the bolus model function. Next, as shown in step 730, the bolus propagation state is determined based on all fitted models. More specifically, the maximum of the DIFF feature curve may be assumed to be the front of the bolus (i.e., "reaching maximum opacity"). Based on a (e.g., linear) fit of the maximum values from a sequence of DIFF feature frames, a future location of the bolus can be predicted. Whether or not the bolus can be tracked may also be determined. For example, recall that the bolus in both the right and left legs are being tracked. Since the vessels of one leg may be diseased, the bolus will move through that leg slower than that of the healthy leg. Consequently, it may become impossible to track the front of the bolus of both legs simultaneously. If this occurs, only the bolus of one leg will be tracked. (Recall, e.g., the bolus tracking mode process 408/600 of FIG. 6.)

Next, as shown in step 740, the vessel characteristics may be updated. For example, if the DIFF feature curve widens, the vessel is more likely to be diseased and, consequently, it may be assumed that the bolus will propagate more slowly through the leg. Accordingly, the bolus tracking strategy may be updated or tuned based on the estimated vessel characteristics.

Finally, at step 750, the bolus location in the next frame is predicted. This prediction may be based on a number of factors including, for example, the DIFF feature curve(s), the DSA feature curve(s), the vessel characteristic, etc. Processing continues at return node 760.

Figure 9:
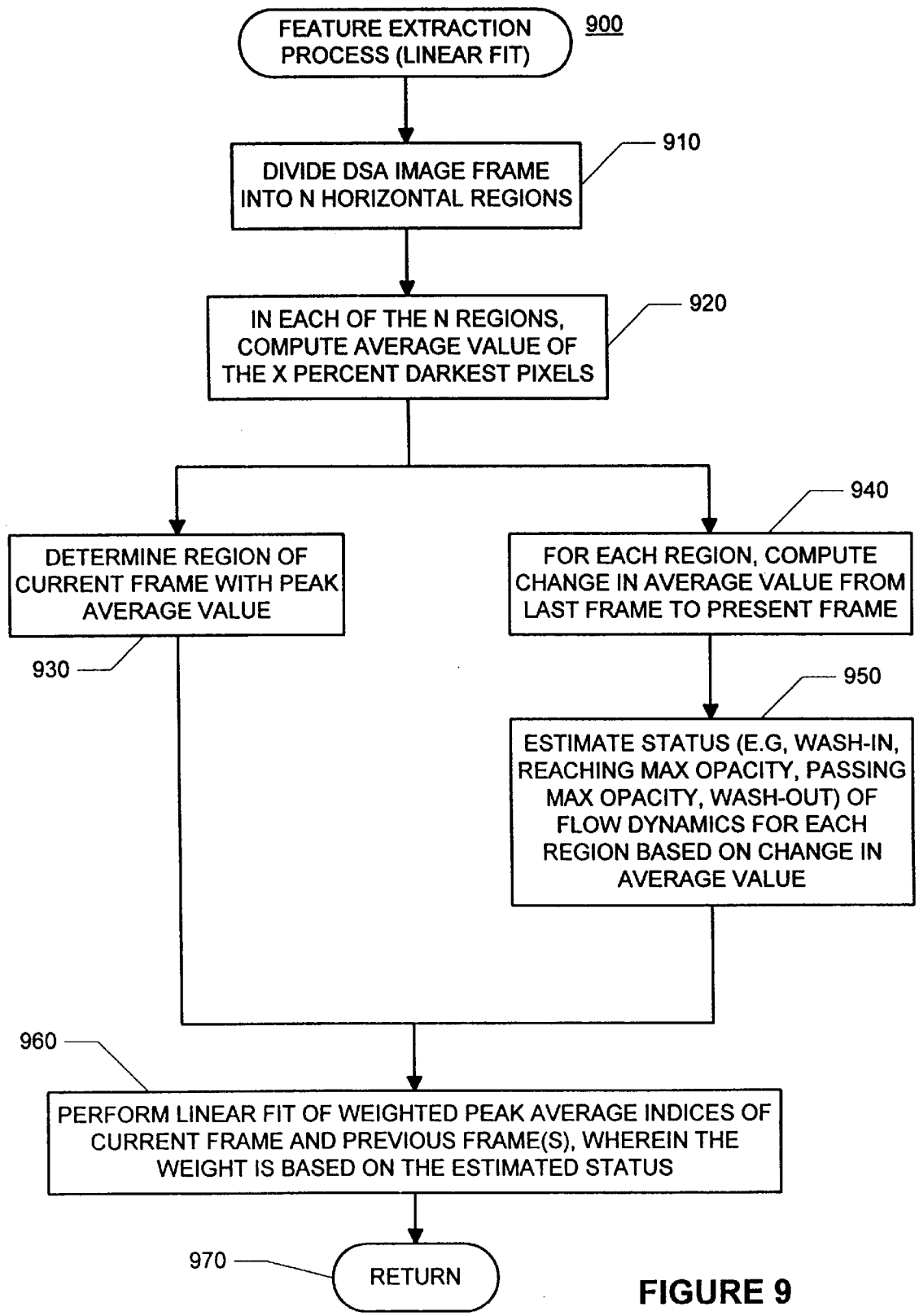
FIG. 9 is a flow diagram of a second embodiment of a feature extraction process of a method of the present invention.

FIG. 9 is a flow diagram of a feature extraction technique 900 which is based on a linear fit of peak image data. First, as shown in step 910, the frame of the DSA image is divided into N (e.g., N=20) horizontal regions. Next, as shown in step 920, in each of the N horizontal regions, the average value of the X (e.g., X=10) percent darkest pixels is computed. The region of the current frame with the peak average value is determined in step 930. In addition, as shown in step 940, for each horizontal region, the change in average value from the previous frame to the present frame is determined.

Thereafter, as shown in step 950, a flow dynamics status is estimated for each region based on the change in average value. The flow dynamics statuses may include "wash-in", "approaching maximum opaqueness", "passing maximum opaqueness", and "wash-out". More specifically, if the change in average value is a large positive value, a wash-in status is assumed; if the change in average value is a small positive value, an approaching maximum opaqueness status is assumed; if the change in average value is a small negative value, a passing maximum opaqueness status is assumed; and if the change in average value is a large negative value, a wash-out status is assumed.

Figure 18:
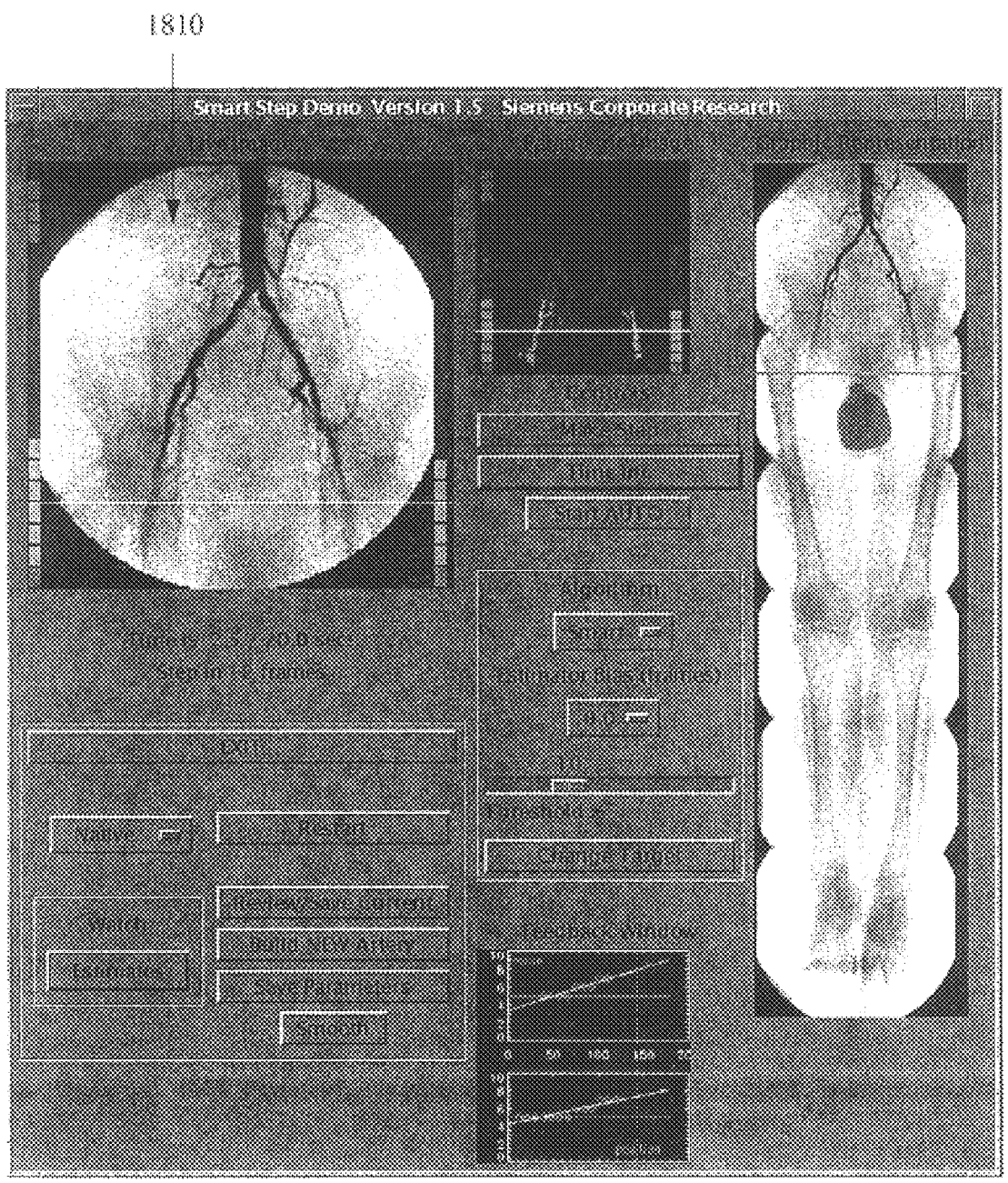
FIG. 18 is a screen of a graphical user interface of a flow status visualization aid process of an apparatus of the present invention.

The estimated flow dynamics status may also be used by the visualization aid process of the present invention. More specifically, as shown in FIG. 18, a parametric image display area 1830 is provided. In this case, the image was divided into twenty (20) horizontal regions. These regions are depicted in different colors, such that the "wash-in" status region(s), if any, is depicted in a first color, the "approaching maximum opaqueness" status region(s), if any, is depicted in a second color, the "passing maximum opaqueness" status region(s), if any, is depicted in a third color, and the wash-out status region(s), if any, is depicted in a fourth color.

Finally, as shown in FIG. 960, the peak average indices of the current frame and previous frames are weighted based on the estimated flow dynamic statuses and a linear fit of these weighted peak averages is performed. The resulting line is used to estimate the bolus location in future frames. Processing continues at return node 970.

Figure 11A:
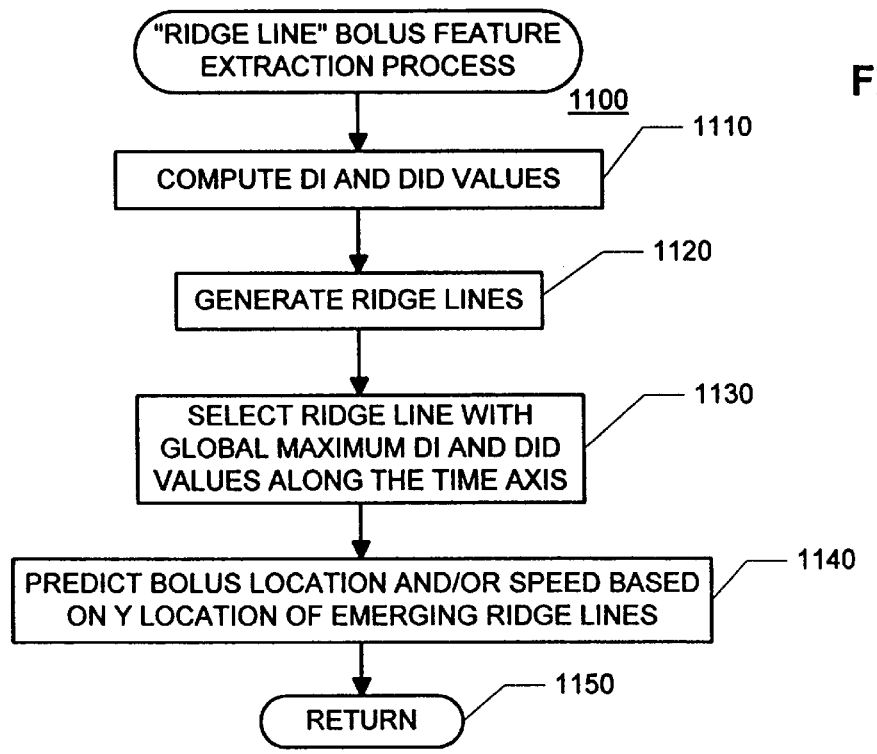
FIG. 11a is a flow diagram of a third embodiment of a feature extraction process of a method of the present invention.
Figure 14A:
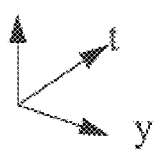
Figure 14A:
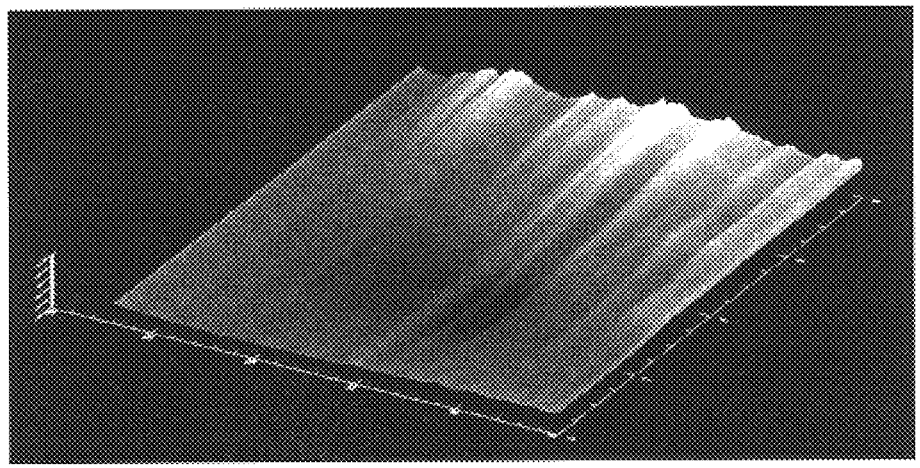

FIG. 11*a* is a high level flow diagram of an alternative bolus feature extraction process 1100 referred to as the "ridge line" feature extraction process. Referring first to step 1110, DI and DID value streams are first computed at various times to form DI and DID arrays. More specifically, the DI image, which is a sum of x pixel values of a DSA image at a particular position "y" and at a particular time "t" can be defined as:

$$DI(y,t) = \Sigma_x[I(x,y,t) - I(x,y,o)] \quad (5)$$

where x is an image pixel index in the direction perpendicular to the y image pixel index. FIG. 14*a* is a three dimensional plot which depicts DI(y,t). A DID image, which is a sum of x pixel values of a DIFF image at a particular position "y" and at a particular time "t" can be defined as:

$$DID(y,t) = \Sigma_x[I(x,y,t) - I(x,y,t-1)] \quad (6)$$

Figure 14B:
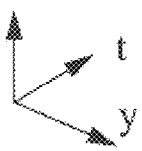
Figure 14B:
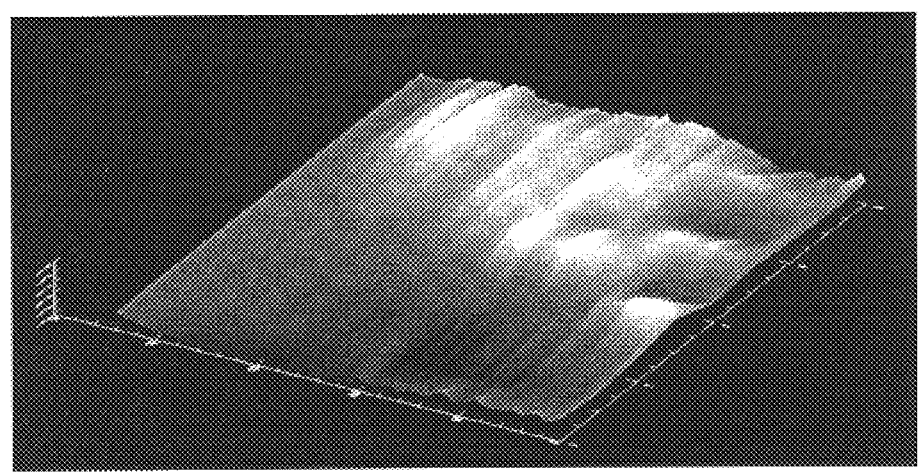

FIG. 14*b* is a three dimensional plot which depicts DID(y,t).

Figure 11B:
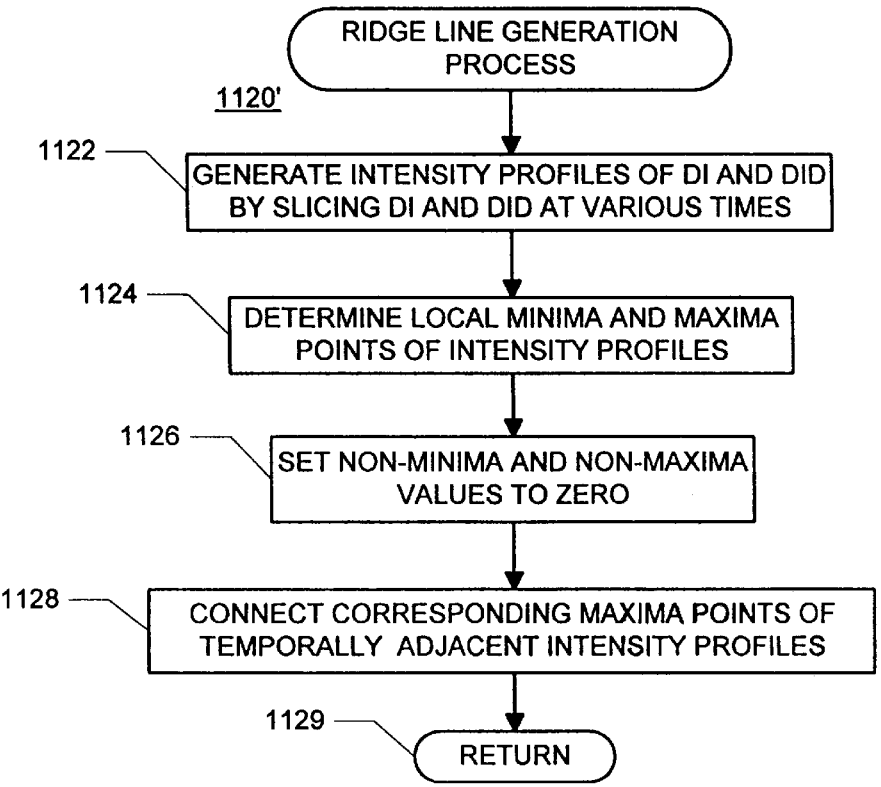
Figure 15:
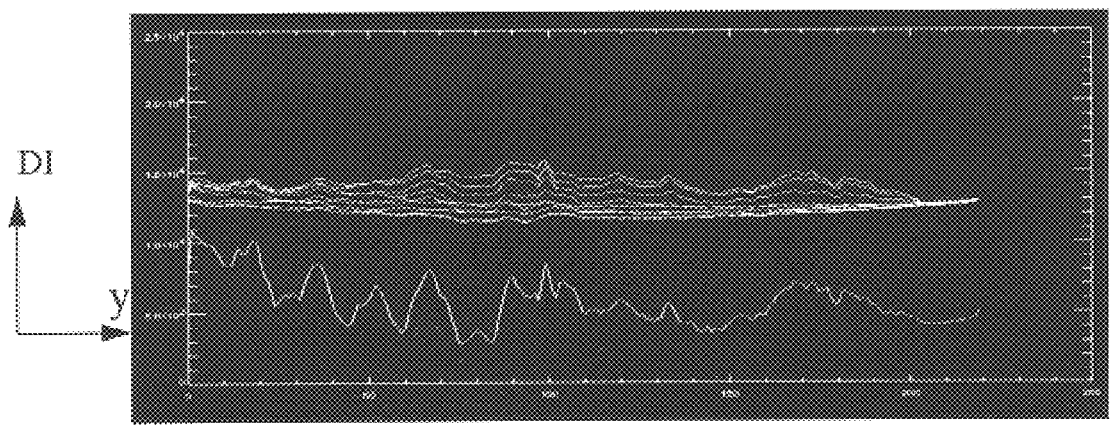
FIG. 15 is a plot of DI(y) at various time slices.

Next, as shown in step 1120, ridge lines are generated. FIG. 11*b* illustrates a process 1120' for generating ridge lines. First, as shown in step 1122, intensity profiles of DI and DID are generated by "slicing" the DI(y,t) and DID(y,t) functions at various times. For example, referring to FIG. 15, each of the plots represents the intensity profile of a DI value as a function of y positions at a particular time. Thereafter, as shown in step 1122, for each time sliced intensity profile, local maxima and minima values of DI(y) and/or DID(y) are determined. At a given time t, this determination may be carried out as follows:

$$\text{local min or max at } y \text{ if } \frac{\partial DI(y, t)}{\partial y} = 0 \quad (7)$$

$$\text{local min or max at } y \text{ if } \frac{\partial DID(y, t)}{\partial y} = 0 \quad (8)$$

Next, as shown in step 1126, non-minima and non-maxima points (y pixels) are set to zero. This may be carried out as follows:

$$\text{if } \frac{\partial DI(y, t)}{\partial y} \neq 0 \text{ at } y, \text{ then set } DI(y, t) \text{ to } 0 \quad (9)$$

$$\text{if } \frac{\partial DID(y, t)}{\partial y} \neq 0 \text{ at } y, \text{ then set } DID(y, t) \text{ to } 0 \quad (10)$$

Finally, as shown in step 1128, corresponding maxima points of temporally adjacent intensity profiles are connected by a line segment. Attached line segments define a ridge line.

Figure 16A:
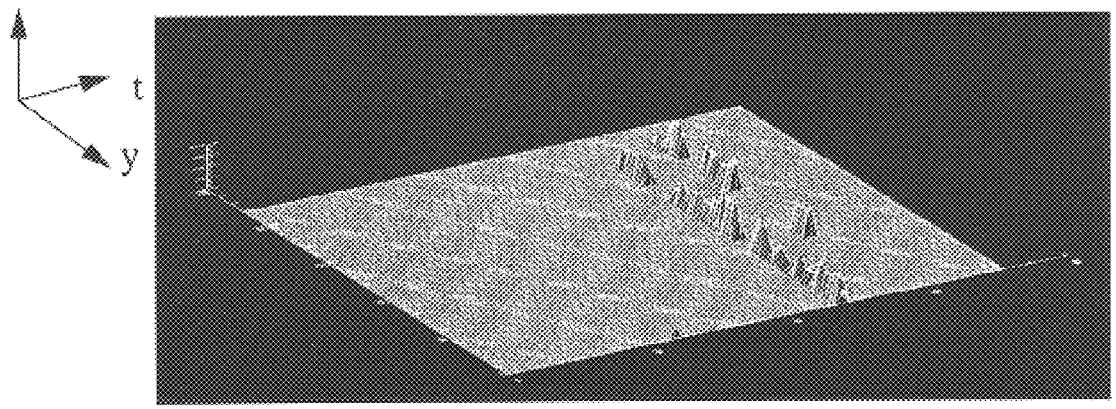
Figure 16B:
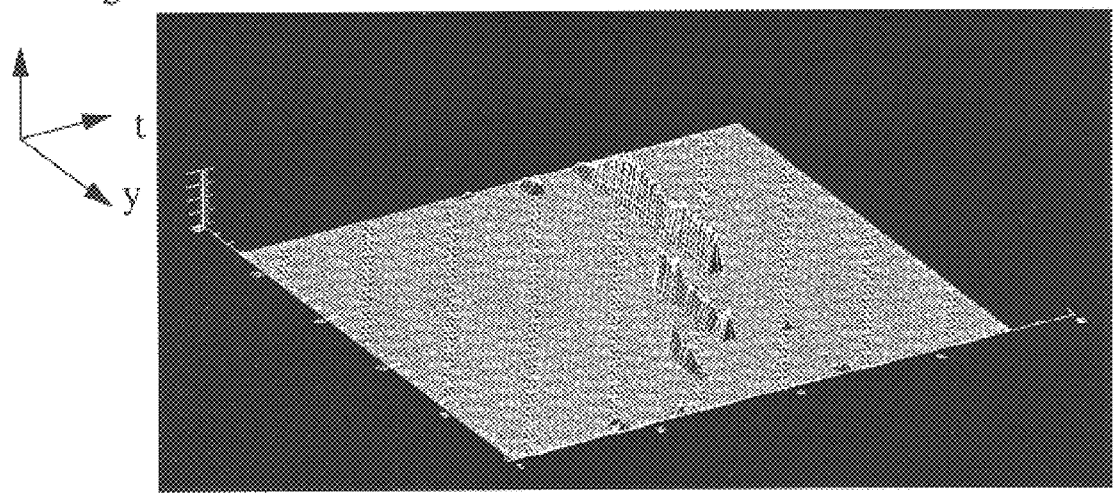

Processing continues at return node 1129. Referring back to FIG. 11a, as shown in step 1130, the ridge line(s) with the global maximum DI and DID values along the time axis are selected. A plot of the global maximum DI values with respect to y and t is depicted in FIG. 16a. Since the DI values are based on a summation of DSA values in the x direction, the plot 16a depicts absolute maximum values. As shown in FIG. 16a, the ridge lines tend to shift from one particular time to another. This is because different segments of local maxima may define the global maximum at different times. Similarly, a plot of the global maximum DID values with respect to y and t is depicted in FIG. 16b. Since the DID values are based on a summation of DIFF values in the x direction, the plot 16b depicts maximum change values. As was the case with FIG. 16a, as shown in FIG. 16b, the ridge lines tend to shift from one particular time to another. Again, this is because difference segments of local maxima may define the global maximum at different times.

The ridge lines of FIGS. 16a and 16b gradually emerge in the y-direction. As shown in step 1140, the bolus location is predicted based on the Y location of the emerging ridge lines. As will be discussed below, a step command may be issued based, at least in part, by the Y location of the emerging ridge line. In particular, when the ridge line of $DID_{max}(y,t)$ (see FIG. 16b) begins to occur at relatively high values of y, it may be assumed that the leading edge of the bolus is reaching the end of the frame of the current gantry station.

Figure 12A:
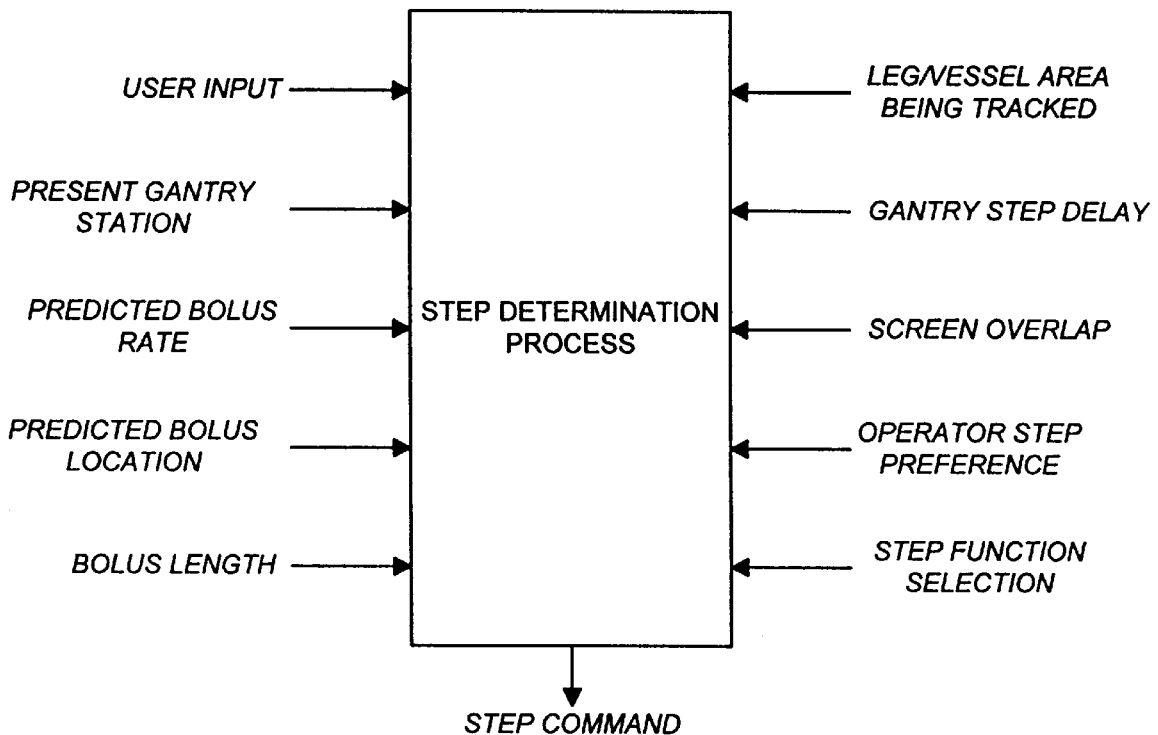
FIG. 12a illustrates possible inputs to, and an output from, a step determination process of the present invention.

Referring now to FIGS. 4 and 12a, a process for performing the step determination step 422 is described. The process for performing step determination may be a function of predetermined settings (e.g., gantry step delay, screen overlap, operator step preference, step function selection, leg vessel area being tracked, etc.), predetermined estimates (e.g., predicted bolus rate, predicted bolus location, bolus length, etc.), estimation updates (e.g., bolus rate, bolus length, etc.), and values determined during the angiographic process (e.g., predicted bolus location, present gantry station, user input, etc.). Basically, the step determination process may be a factor of any one of, or a combination of any of, the above values. However, the step determination process will almost always consider the predicted bolus location (e.g., the location of the plateau or the front of the bolus). Whether or not the user input is considered will depend upon the step function selection. (See, e.g., FIGS. 20a through 20d.) Regardless of the factors considered, the step determination process will provide an output from which it can be determined whether or not to step the imaging unit 110/111 (and/or table) to the next station.

Figure 12B:
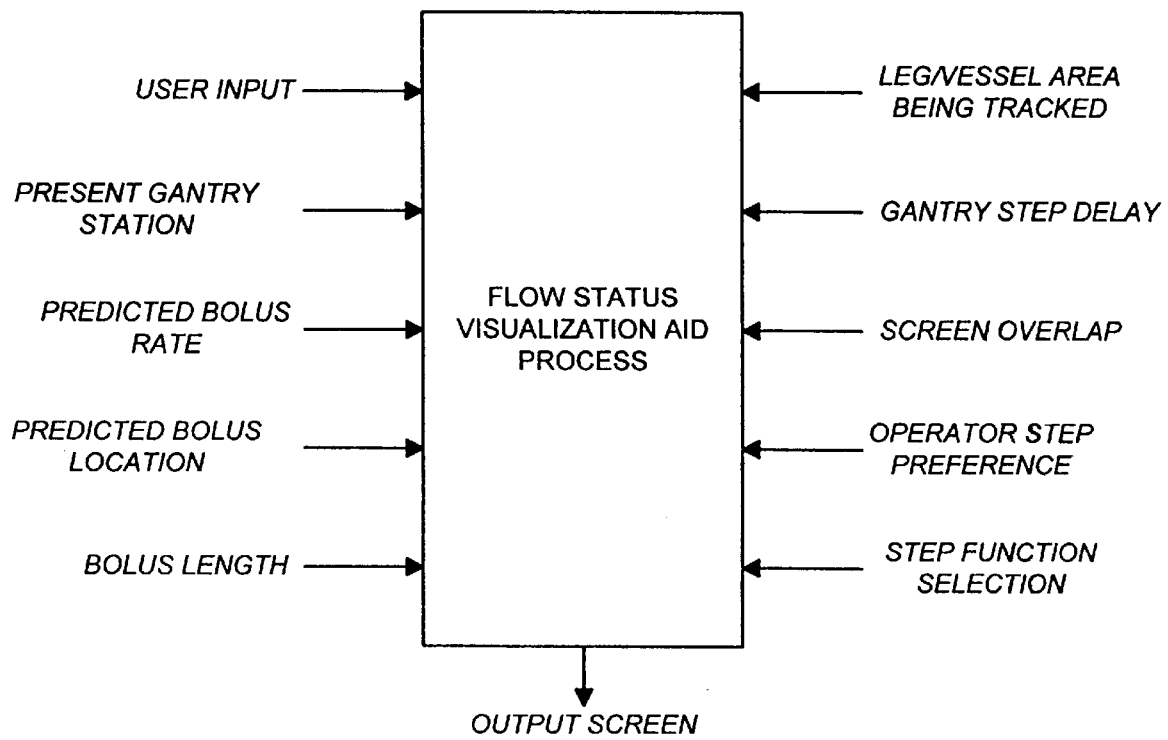
FIG. 12b illustrates possible inputs to, and an output from, a flow status visualization aid process of the present invention.
Figure 13:
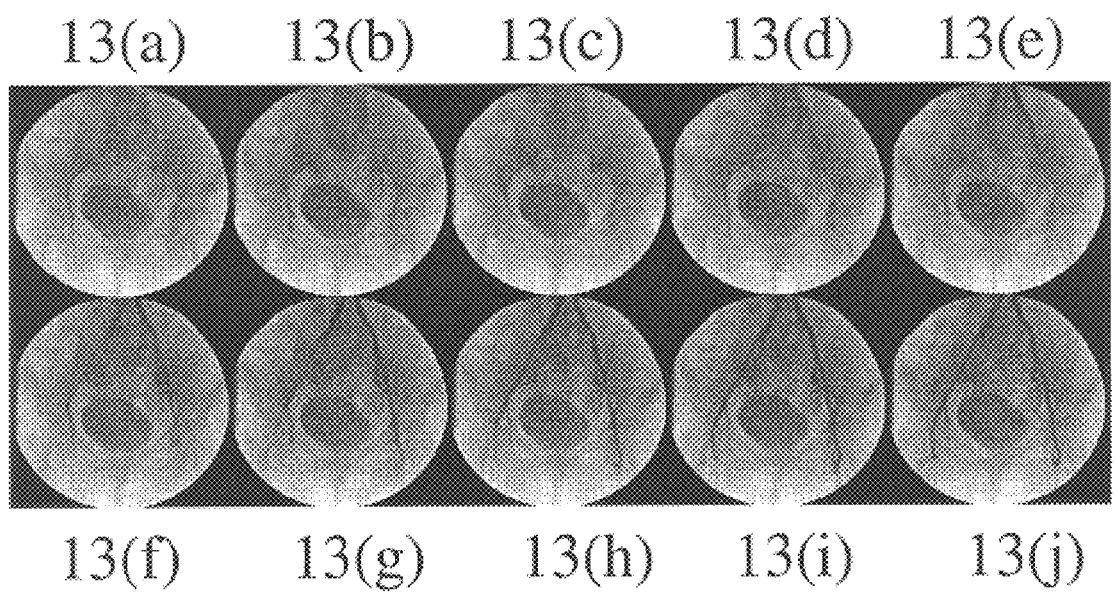
FIGS. 13a–13j illustrate a sequence of image frames acquired at a particular gantry station.

Referring to FIGS. 4 and 12b, a flow status visualization aid process for performing the step of providing user visualization output 418 may use similar factors to provide visual output data for assisting an operator in deciding when to step. The visual output data may be in the form of (a) a suggestion to step (See, e.g., the "Step in_frames" line 1822 of the user interface display screen 1800 of FIG. 18.), (b) color coded flow dynamics status as discussed above with reference to the parametric image window 1830 of FIG. 18, (c) extracted DSA features of the left and right legs (See, e.g., plots 1740 and 1750, respectively, of FIGS. 17a through 17f.), and/or (d) extracted DIFF features of the left and right legs (See, e.g., plots 1760 and 1770, respectively, of FIGS. 17a through 17f.) The feedback window 1860 may also be used as a visual aid but is believed to be more useful for off-line analysis of training exercises.

Figure 19:
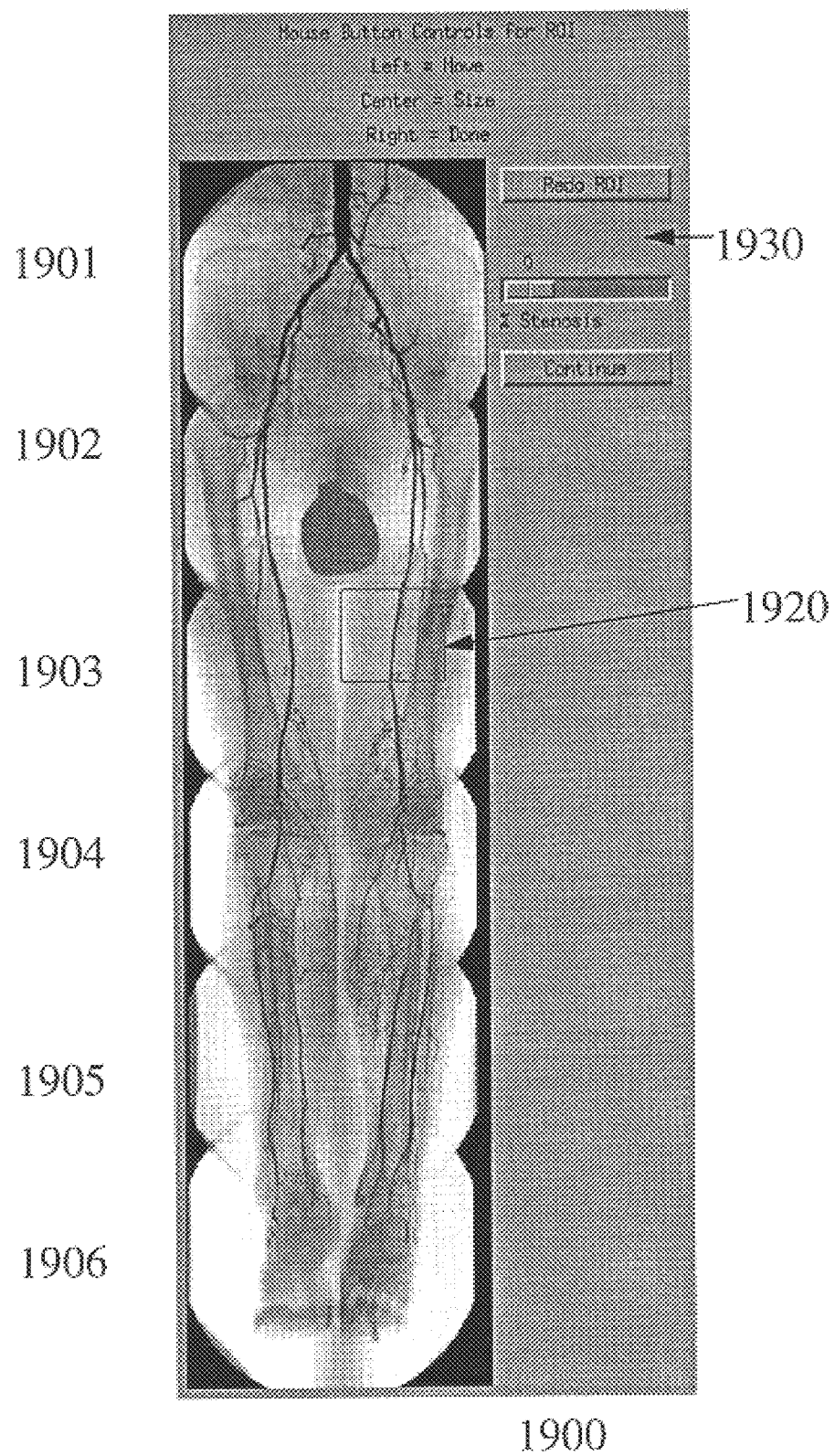
FIG. 19 is a screen of a graphical user interface for creating angiographic training simulations in an apparatus of the present invention.
Figure 21:
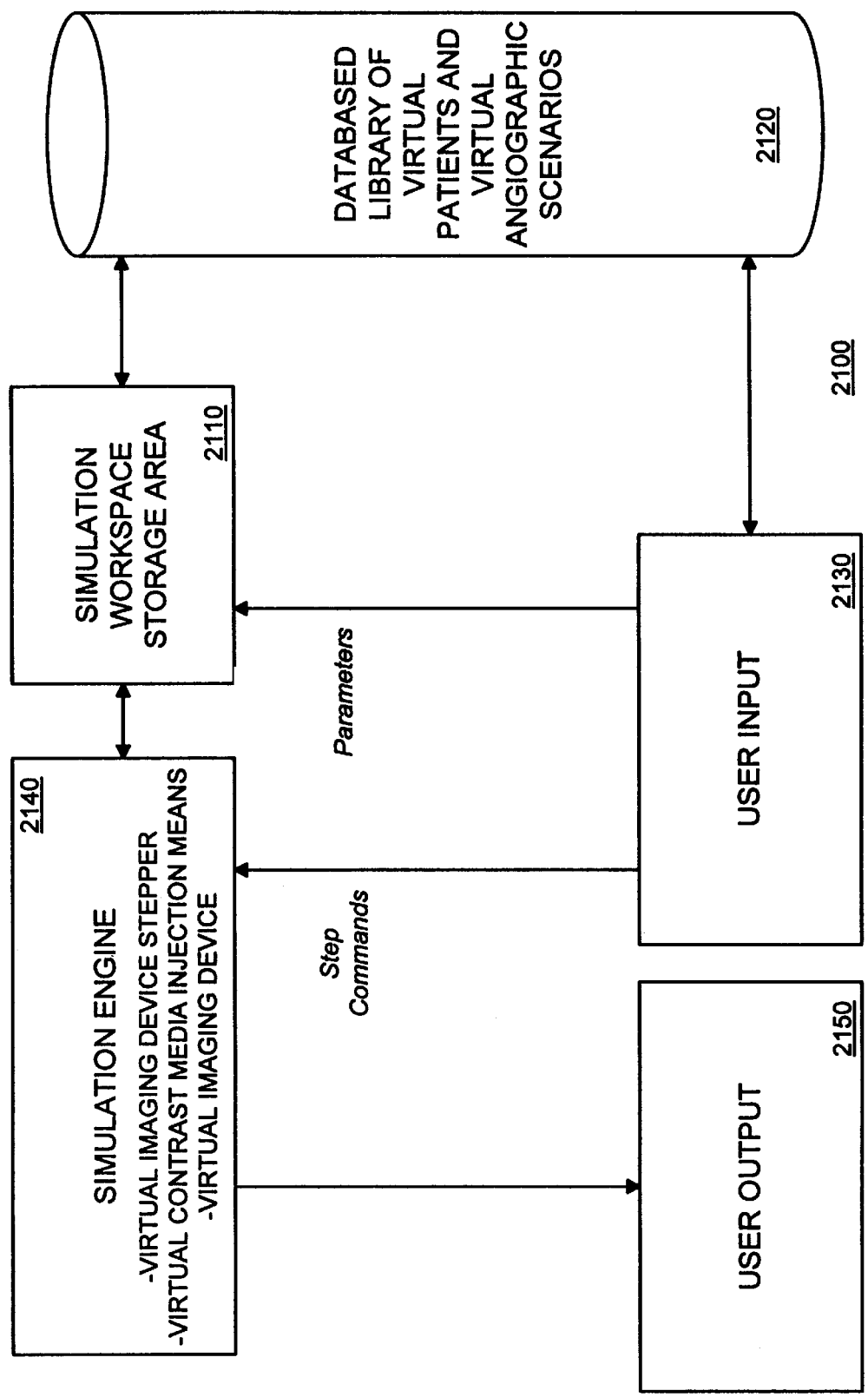
FIG. 21 is a high level block diagram of an apparatus for training angiographers and for planning an angiographic procedure in accordance with the present invention.

As was discussed above, the present invention may also be used to simulate an angiographic imaging process. FIG. 21 is a high level block diagram of a system 2100 for simulating an angiographic process. The system 2100 may include a simulation workspace storage area 2110, a databased library of virtual patients and virtual angiographic scenarios 2120, an user input device 2130, a simulation engine 2140, and an user output device 2150. The databased library 2120 includes a number of virtual patients, each having different vessel conditions. A selected virtual patient is loaded into the simulation workspace storage area 2110. Here, the vessel conditions of the virtual patient may be modified via the user input device 2130. A "virtual patient" may be generated with a graphical user interface 1900 of FIG. 19. Such a process may be invoked via the "Build NEW Artery" button of screen 1800 of FIG. 18. As shown in FIG. 19, six partially overlapping images 1901 through 1906 may be used to image the bolus flow through a patient's legs. A window 1920, the size and location of which may be controlled by a user, may be used to simulate stenosis (e.g., restricted blood flow) in certain region(s) of the legs. The extent of the stenosis within the window 1920 is determined based on the position of the slider 1930.

Figure 8:
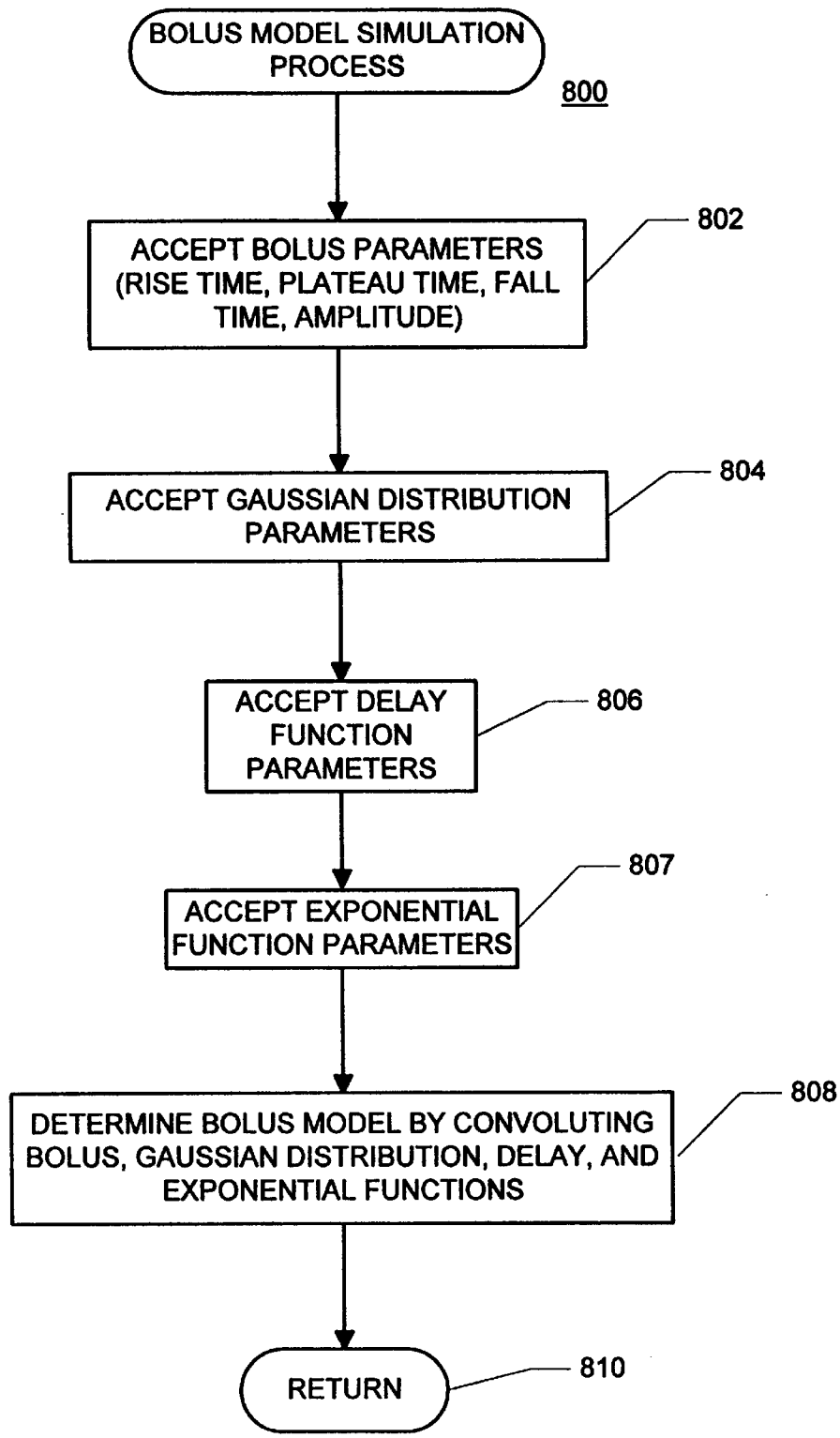
FIG. 8 is a flow diagram of a bolus model determination process which may be used in training simulations.
Figure 10:
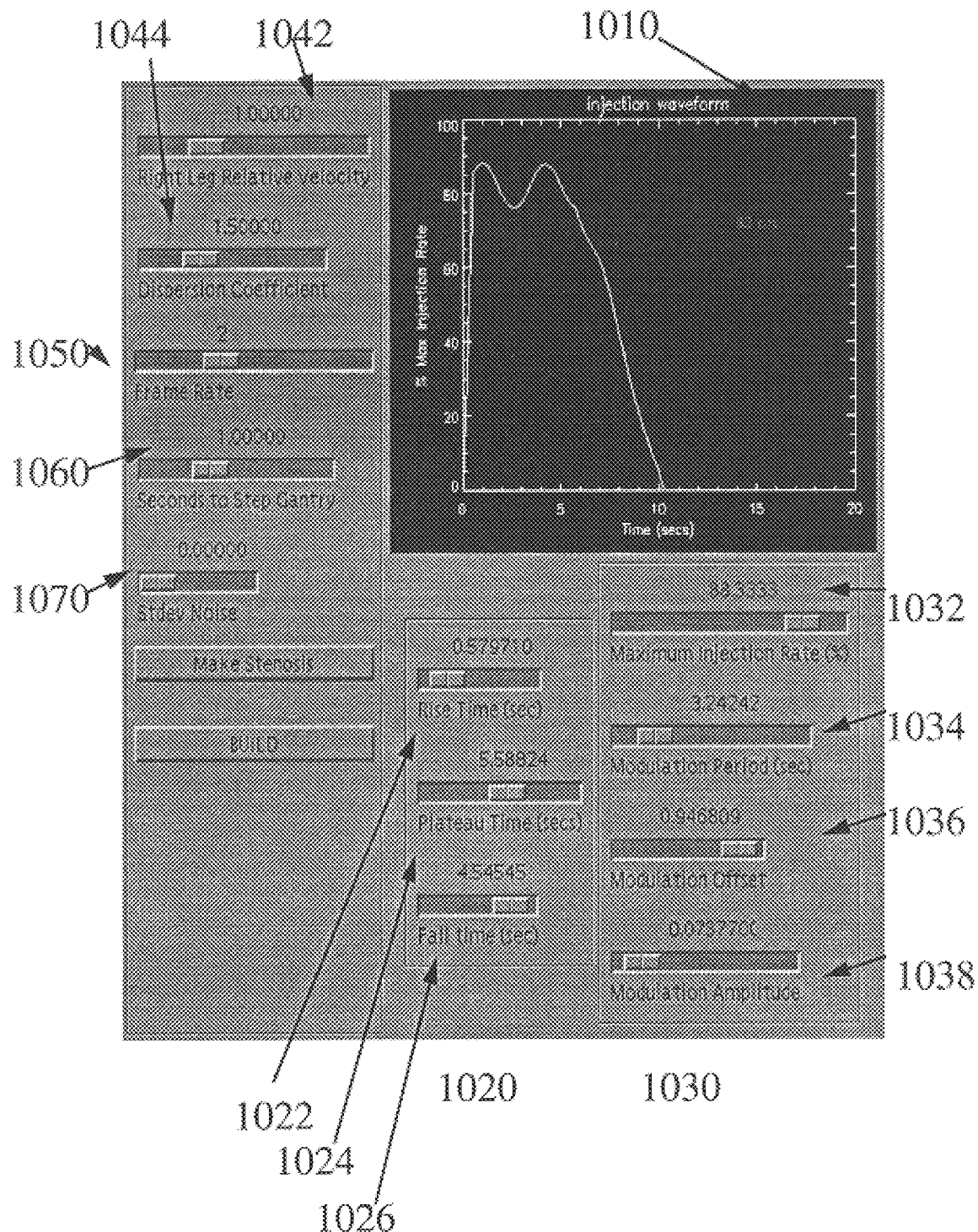
FIG. 10 is a screen, for providing simulation and bolus model settings, of a graphical user interface of an apparatus of the present invention.

FIG. 8 is a flow diagram of a bolus model determination process 800 which may be used in a simulation of an angiographic procedure. As shown in step 802, parameters for the simple bolus function are accepted. Referring to the user interface screen 1000 of FIG. 10, the parameters of the simple bolus function may include a rise time 1022, a plateau time 1024, a fall time 1026, a maximum injection rate (i.e., the amplitude of the plateau) 1032, a modulation period 1034, a modulation offset 1036, and a modulation amplitude 1038. As shown in FIG. 10, a display area 1010 displays a plot of the simple bolus function based on the parameter settings. As shown in steps 804, 806 and 807, parameters for a gausian distribution function, a delay function, and an exponential function, respectively, are also accepted. Thereafter, as shown in step 808, a bolus model is determined by convoluting the bolus function, the Gausian distribution function, the delay function, and the exponential function. Processing continues at return node 810.

A virtual angiographic scenario may also be loaded into the simulation workspace storage area 2110 and may also be modified by the user input device 2130.

The simulation engine simulates the image capture unit, the stepping unit and the contrast media injection means which act upon the virtual patient and the virtual angiographic scenario stored in the simulation workspace storage area 2110. Parameters of the virtual image capture unit, virtual stepping unit, and virtual contrast media injection means may be modified via the user input device 2130. The simulation engine accepts step commands from the user input unit 2130 and provides display data to the user output unit 2150.

Thus, the present invention also provides an off-line apparatus for training inexperienced angiographers, residents, fellows, etc. This aspect of the present invention may also be used as a planning aid in which, before an actual angiographic procedure, the angiographer may run simulated tests with different volumes of contrast media, different injection rates or patterns, different stepping times, etc. on a virtual patient to which the actual patient is believed to be similar. In this way, the actual angiographic procedure may be optimized.

Since the training and planning aspects of the present invention do not require real patients, or real stepping and imaging units, such training and planning will not tie up expensive resources that are typically in high demand. Indeed, such training and planning need not even occur in a hospital.

Having described an exemplary system and exemplary methodologies for practicing the present invention, an example of the operation of the system and methodologies of the present invention are now provided.

FIGS. 13a through 13j depict a sequence of frames of angiographic images at a first gantry station. As ca be seen from the sequence of frames, the bolus (or contrast media) flows downward from the torso to the feet. Similarly, FIGS. 17a through 17f depict screens 1700 of a graphical user interface which show, inter alia, a sequence of contrast frames 1710. The screens also illustrate the DSA frame 1720, the DIFF frame 1730, an extracted DSA feature of the left leg (or side) 1740, an extracted DSA feature of the right leg (or side) 1750, an extracted DIFF feature of the left leg (or side) 1760, and an extracted DSA feature of the right leg (or side) 1770. In FIGS. 17a through 17f, it is assumed that the fitted bolus model feature extraction process (see FIGS. 7 and 8) was used. More specifically, in the left and right DIFF feature windows (1760 and 1770, respectively), the fitted bolus model is depicted in dot-dash lines. It is further assumed that the images were divided into twenty (20) regions.

Figure 17A:
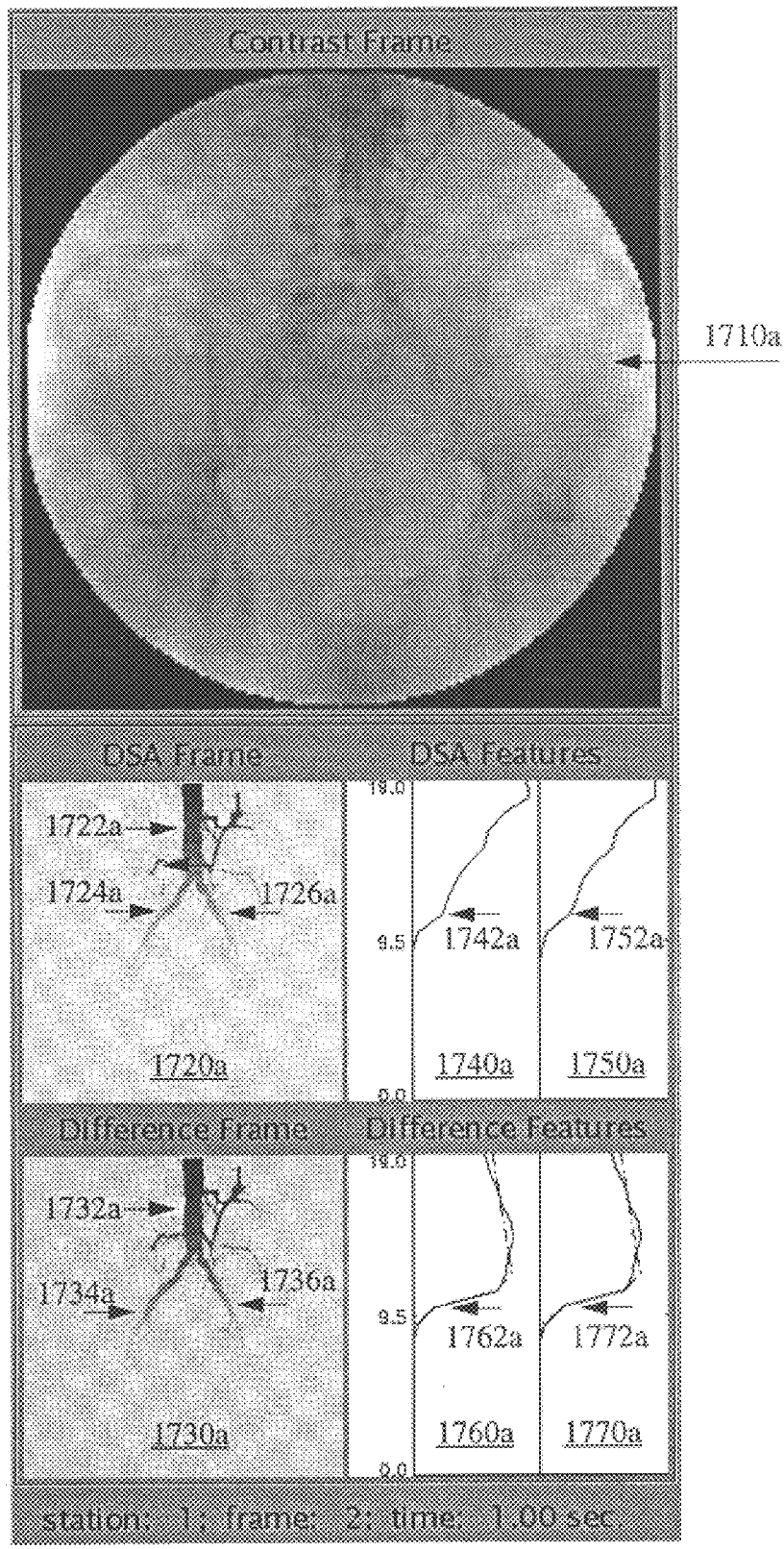
FIGS. 17a–17f illustrate screens, which depict a sequence of frames, of a graphical user interface of an apparatus of the present invention.
Figure 17B:
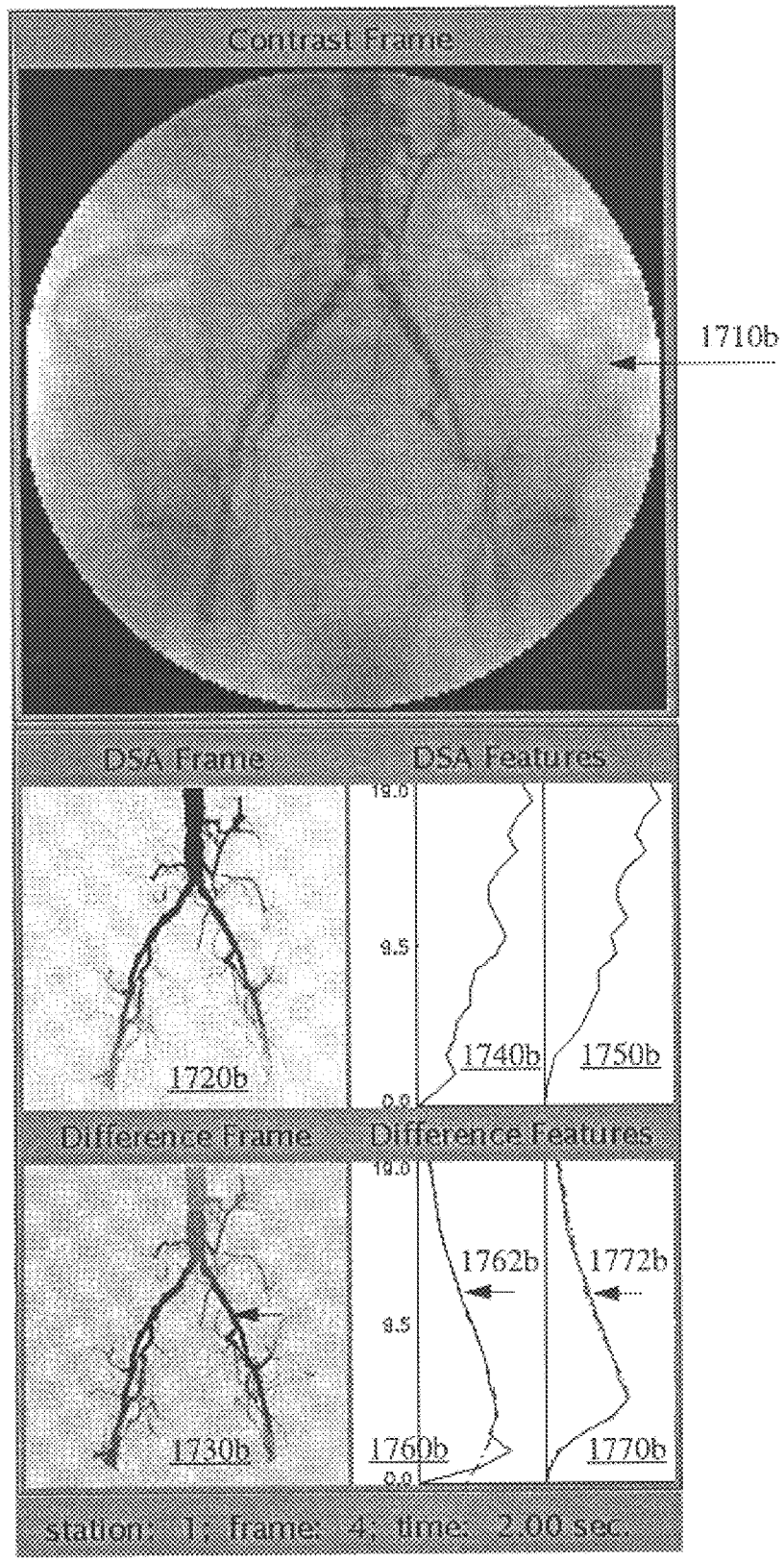
Figure 17C:
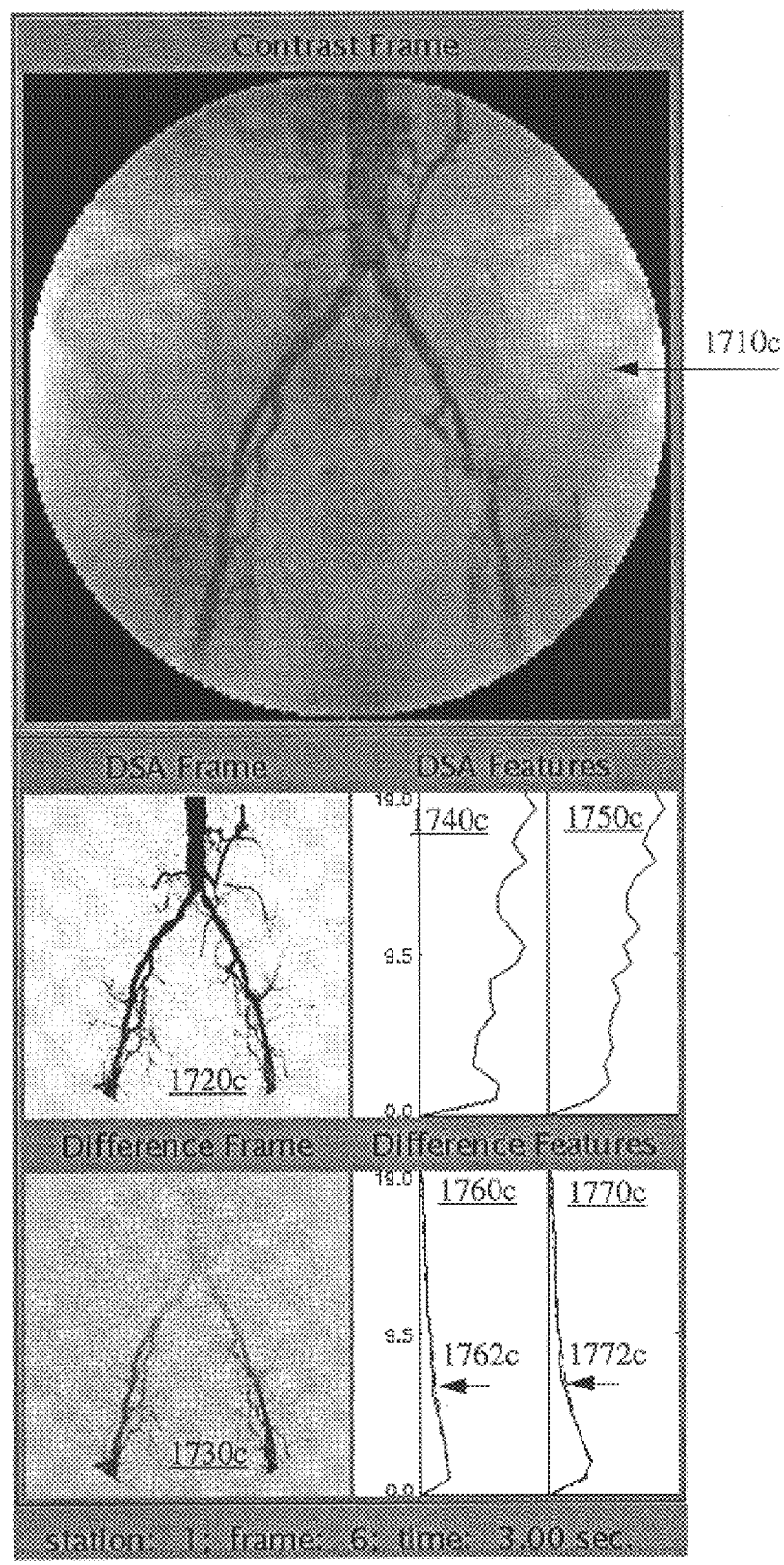
Figure 17D:
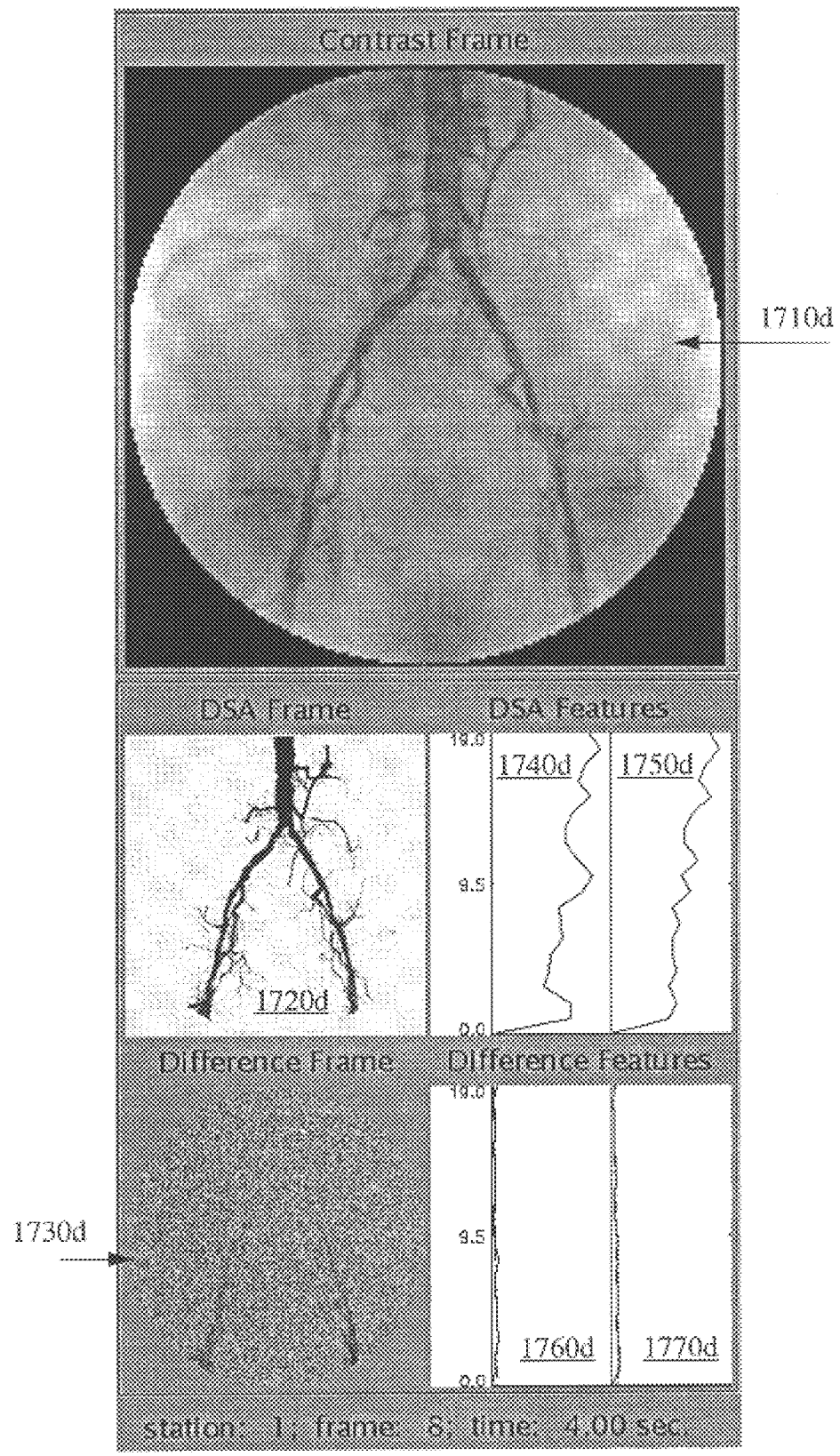
Figure 17E:
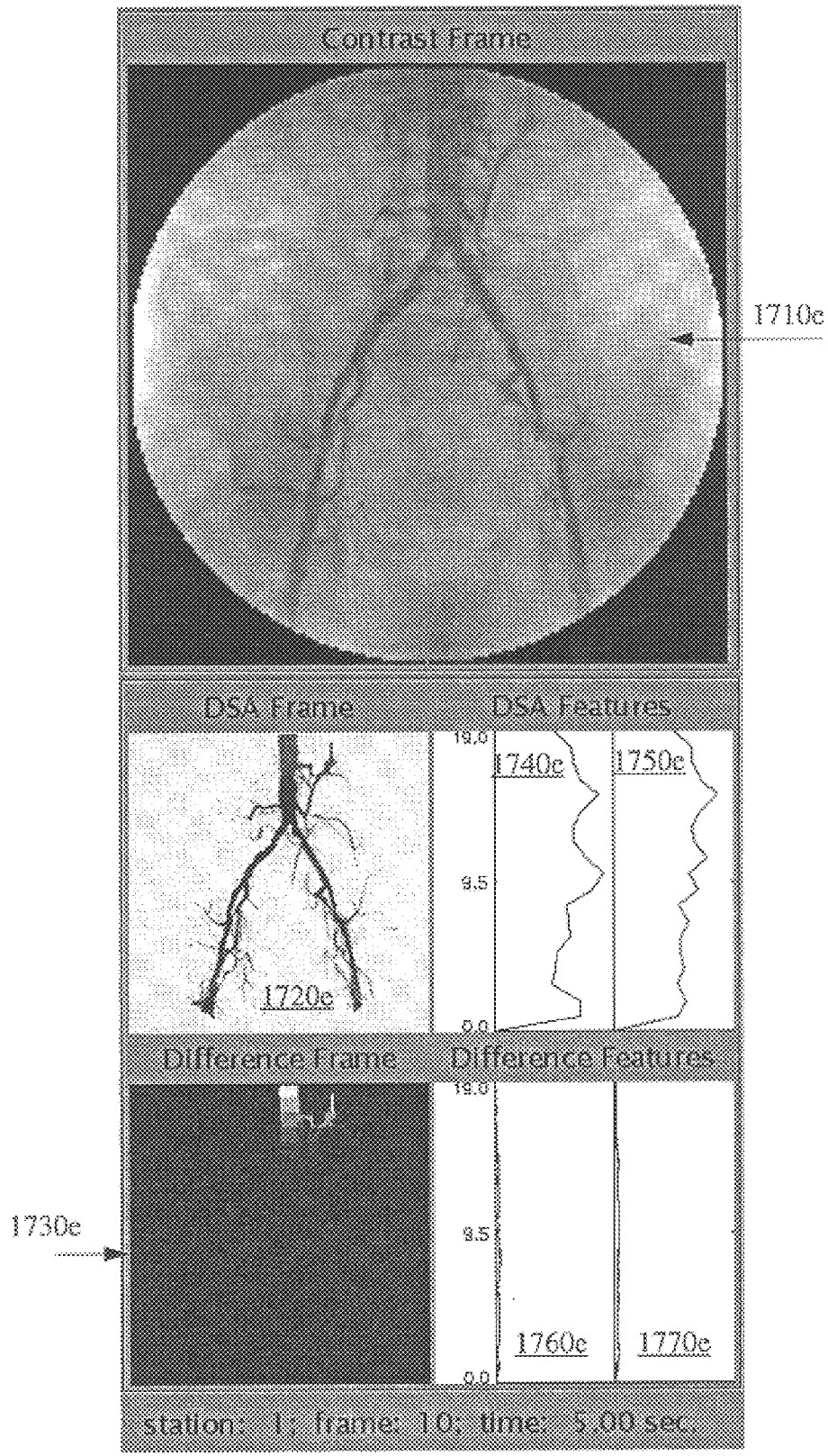
Figure 17F:
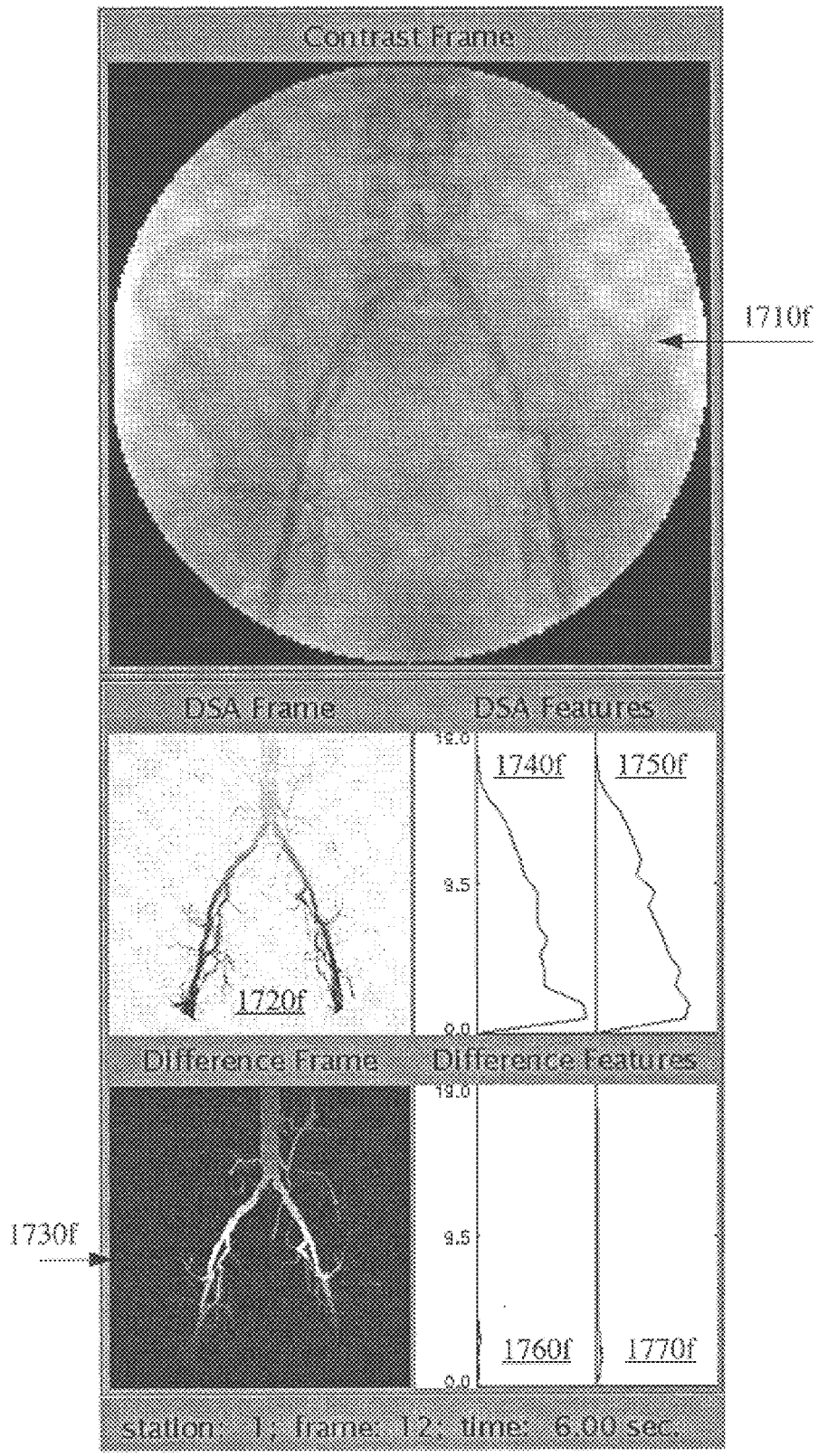

Referring now to the left and right DIFF feature display areas 1760a and 1770a, respectively, of FIG. 17a, the leading edge of the bolus 1762a and 1772a in the left and right legs, respectively, are easily visualized. As shown in FIG. 17b, the leading edge of the bolus 1762b and 1772b is almost at the end of the image. Ideally, assuming an almost instantaneous stepping time, the imaging device 110/111 (and/or table) would be stepped at about this time. Next, as shown in FIG. 17c, the left and right bolus have begun to reach maximum opacity as shown in areas 1766c and 1776c, respectively. Thereafter, the plateau region of the bolus opacity can be appreciated from the DIFF images 1730, the DIFF features of the left leg 1760, the DSA features of the left leg 1740, the DIFF features of the right leg 1770, and the DSA features of the right leg 1750 shown in FIGS. 17d and 17e. Thus, the DSA images 1720 of FIGS. 17d and 17e show that the contrast media continues to provide good opacity; the opacity depicted by the DSA image 1730, the DSA features of the left leg 1740, and the DSA features of the right leg 1750, only begins to fade (i.e., bolus wash-out) in FIG. 17f. However, in this example, the DIFF features extracted are more important since they indicate will permit the capture of images with the maximum opacity and will not require as made images to be gathered.

What is claimed is:

1. A visualization aid for use with an imaging system including an imaging device, means for stepping the imaging device relative to a patient, and a contrast media injection means, the visualization aid comprising:
   a) an input for receiving images from the imaging device;
   b) means for extracting features from images received at the input to generate extracted features;
   c) means for determining a video output based, in part, on flow dynamics of a bolus estimated from the extracted features; and
   d) an output for providing the video output; wherein the means for extracting features includes:
      i) means for determining a DSA (digital subtraction angiographic) image;
      ii) means for sectioning the DSA image into horizontal regions;
      iii) means for, in each of the regions of the DSA image, determining an average value of a predetermined percentage darkest pixels;
      iv) means for determining a region of the DSA frame with a peak average value;
      v) means for, in each of the regions of the DSA frame, computing a change in its average value from a previous DSA frame;
      vi) means for, in each of the regions of the DSA frame, estimating a flow dynamics status based on the change in average value;
      vii) means for weighting the peak average value of the DSA frame based on the estimated flow dynamics status; and
      viii) means for fitting the weighted peak average value of the DSA frame and that of the previous DSA frame to a function.

2. The visualization aid of claim 1 wherein the function is a linear function.

3. The visualization aid of claim 1 wherein the video output is based on the estimated flow dynamics status of each region.

4. The visualization aid of claim 3 wherein the estimated flow dynamics statuses include (a) "wash-in", (b) "approaching maximum opacity", (c) "passing maximum opacity", and (d) "wash-out", and
   wherein the video output provides a distinct color for each of the estimated flow dynamics statuses.

5. The visualization aid of claim 1 further comprising means for generating data for displaying DSA features.

6. The visualization aid of claim 1 further comprising means for generating data for displaying DIFF (difference) features.

7. A program storage device readable by a machine, tangibly embodying a program of instructions executable by the machine to perform method steps for providing visual aid in an imaging system, the method steps comprising:
   a) receiving images from an imaging device;
   b) extracting features from the received images to generate extracted features;
   c) determining a video output based, in part, on flow dynamics of a bolus estimated from the extracted features; and
   d) outputting the video output;
   wherein the instructions for extracting features comprise instructions for:
      I) determining a DSA image;
      ii) sectioning the DSA image into horizontal regions;
      iii) in each of the regions of the DSA image, determining an average value of a predetermine percentage darkest pixels;
      iv) determining a region of the DSA frame with a peak average value;
      v) in each of the regions of the DSA frame, computing a change in its average value from a previous DSA frame;
      vi) in each of the regions of the DSA frame, estimating a flow dynamics status based on the change in average value;
      vii) weighting the peak average value of the DSA frame based on the estimated flow dynamic status; and viii) fitting the weighted peak average value of the DSA frame and that of the previous DSA frame to a function.

8. The program storage device of claim 7, wherein the function is a linear function.

9. The program storage device of claim 7, wherein the video output is based on the estimated flow dynamics status of each region.

10. The program storage device of claim 9, wherein the estimated flow dynamics statuses include (a) "wash-in", (b) "approaching maximum opacity, "passing maximum opacity", and (d) "wash-out".

11. The program storage device of claim 10, wherein the video output provides a distinct color for each of the estimated flow dynamics statuses.

12. The program storage device of claim 7, further comprising instructions for generating data for displaying DSA features.

13. The program storage device of claim 7, further comprising instructions for generating data for displaying DIFF (difference) features.

14. A method for providing visual aid in an imaging system, comprising the steps of:
   a) receiving images from an imaging device;
   b) extracting features from the received images to generate extracted features;
   c) determining a video output based, in part, on flow dynamics of a bolus estimated from the extracted features; and
   d) outputting the video output; wherein the step of extracting features comprises the steps of:
      I) determining a DSA image;
      ii) sectioning the DSA image into horizontal regions;
      iii) in each of the regions of the DSA image, determining an average value of a predetermine percentage darkest pixels;
      iv) determining a region of the DSA frame with a peak average value;
      v) in each of the regions of the DSA frame, computing a change in its average value from a previous DSA frame;
      vi) in each of the regions of the DSA frame, estimating a flow dynamics status based on the change in average value;
      vii) weighting the peak average value of the DSA frame based on the estimated flow dynamic status; and
      viii) fitting the weighted peak average value of the DSA frame and that of the previous DSA frame to a function.

* * * * *